United States Patent
Zeligs et al.

(10) Patent No.: US 12,171,745 B2
(45) Date of Patent: Dec. 24, 2024

(54) COMPOSITIONS AND METHODS FOR TREATING NON-HEMORRHAGIC CLOSED HEAD INJURY

(71) Applicant: Boulder BioScience LLC, Boulder, CO (US)

(72) Inventors: Michael A. Zeligs, Boulder, CO (US); Irwin C. Jacobs, Defiance, MO (US)

(73) Assignee: Boulder BioScience LLC, Boulder, CO (US)

( * ) Notice: Subject to any disclaimer, the term of this patent is extended or adjusted under 35 U.S.C. 154(b) by 0 days.

(21) Appl. No.: 18/475,838

(22) Filed: Sep. 27, 2023

(65) Prior Publication Data

US 2024/0131005 A1  Apr. 25, 2024

Related U.S. Application Data

(60) Provisional application No. 63/377,834, filed on Sep. 30, 2022.

(51) Int. Cl.
*A61K 31/404* (2006.01)
*A61K 45/06* (2006.01)
*A61P 25/00* (2006.01)

(52) U.S. Cl.
CPC ............ *A61K 31/404* (2013.01); *A61K 45/06* (2013.01); *A61P 25/00* (2018.01)

(58) Field of Classification Search
CPC ........ A61K 31/404; A61K 45/06; A61P 25/00
See application file for complete search history.

(56) References Cited

U.S. PATENT DOCUMENTS

| | | |
|---|---|---|
| 7,348,352 B2 | 3/2008 | Zeligs |
| 7,989,486 B2 | 8/2011 | Zeligs |
| 8,080,577 B2 | 12/2011 | Zeligs |
| 8,236,848 B2 | 8/2012 | Zeligs |
| 8,552,052 B2 | 10/2013 | Zeligs |
| 8,586,621 B2 | 11/2013 | Zeligs |
| 9,353,058 B2 | 5/2016 | Zeligs |
| 9,663,462 B2 | 5/2017 | Zeligs |
| 9,928,965 B2 | 3/2018 | Zeligs et al. |
| 10,441,569 B2 | 10/2019 | Zeligs et al. |
| 10,799,479 B2 | 10/2020 | Zeligs et al. |
| 11,160,834 B2 | 11/2021 | Prockop et al. |
| 11,337,961 B2 | 5/2022 | Zeligs et al. |
| 11,529,331 B2 | 12/2022 | Zeligs et al. |
| 2020/0138919 A1 | 5/2020 | Inserm et al. |
| 2022/0280479 A1 | 9/2022 | Zeligs et al. |
| 2023/0104863 A1 | 4/2023 | Zeligs et al. |

FOREIGN PATENT DOCUMENTS

WO  2015042170 A1  3/2015

OTHER PUBLICATIONS

Rzemienic et al., Apoptosis, 2019, 24:435-52.*
Bo Dam Lee et al., Antioxidants, 2020, 9, 3.*
De Miranda et al., J. Pharmacol. Exp. Therap., 2013, 345: 125-33.*
Cifu Brain Injury, 2022, 36(5), 587-597.
Fenn, et al. J. Neurotrauma 2015, 32, 127-138.
Giordano, et al. Exp. Neurobio. 2022, 31(2), 105-115.
Matsumoto, et al. J. Neuroimmunology 2020, 342, 577195.
Meyer, et al. Exper. Neurology 2012, 235, 574-587.
Miller, et al. Med. Care. 2021, 59(5), 451-455.
Mondello, et al. Cells 2020, 9, 977.
Phelps, et al. Neurorehab. Neuronal Repair 2017, 31(1), 25-33.
Ramakrishna, et al. Eur. J. Pharmacol. 2022, 919, 174812.
Reger, et al. Biol. Psychiatry. 2012, 71(4), 335-343.
Schallert, et al. Neuropharmacol. 2000, 39, 777-787.
Thompson, et al. J. Neurotrauma 2005, 22(1), 42-75.
Zhao, et al. Protein Cell 2017, 8(11), 801-810.
Anderton, et al. Clin. Cancer Res. 2004, 10, 5233-5241.
Olsen, et al. Front. Oncol. 2014, 4, art. 105.
Almieda, et al. J. Polymer Res. 2018, 25, 31.
Coumans, et al. Circul. Res. 2017, 1632-1648.
Blaya et al. J. Neurotrauma 2014, 31, 476-486.
Floyd et al. J. Neurotrauma 2002, 19(3), 303-316.
Harris et al. Front. Cell. Neurosci. 2023, 17, 1055455.
Kim et al. Toxicol. Sci. 2014, 137(1), 158-167.
Li et al. The FASEB J. 2021, 35, e21617.
Lyeth et al. Brain Res. 1992, 569, 281-286.
Marklund et al. Br. J. Pharmacol. 2011, 164, 1207-1229.
Oliva et al. Neurosci. 2011, 180, 272-279.
Titus et al. Exp. Neurol. 2015, 263, 254-262.
Tsuda et al. NeuroReport 2016, 27, 724-729.
Wee et al. Molecules 2024, 29, 1470.
Ziogas et al. J. Neurosci. 2018, 38(16), 4031-4047.
Clearfield, William Nat "The Endocrinology of Traumatic Brain Injury" [online] Sep. 29, 2018 (Sep. 29, 2018) [retrieved on Jan. 17, 2024]. Retrieved from the Internet: <URL: https://drclearfield.net/wp-content/uploads/2018/10/7.-The-Endocrinology-of-Traumatic-Brain-Injury.pdf> pp. 1-244 (p. 217); XP093112407.

* cited by examiner

*Primary Examiner* — Olga N Chernyshev
(74) *Attorney, Agent, or Firm* — Rimon, P.C.; Dale L. Rieger

(57) ABSTRACT

Provided herein are methods of treating non-hemorrhagic closed head injury (NHCHI) with 3,3'-diindolylmethane or an analog thereof. In one embodiment, NHCHI covers Traumatic Brain Injuries (TBIs) including mild to severe concussion, blast injury due to proximity to explosions, cerebral contusion, coup-contrecoup injury, DAI, Second Impact Syndrome, or CHI associated with deceleration injury.

16 Claims, 10 Drawing Sheets

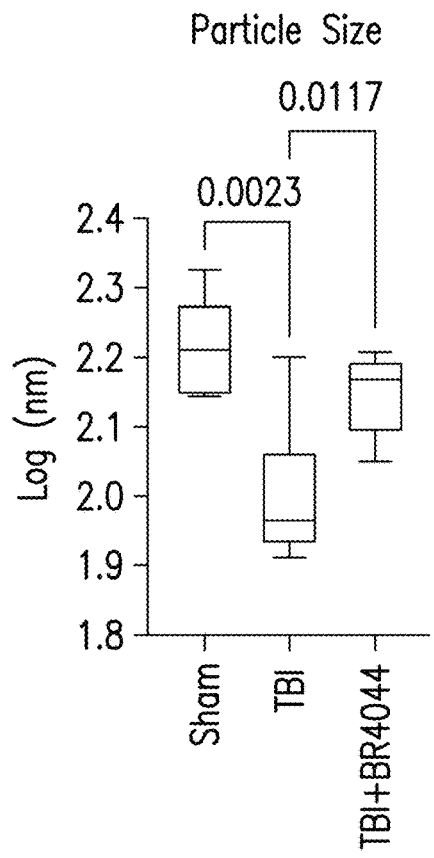
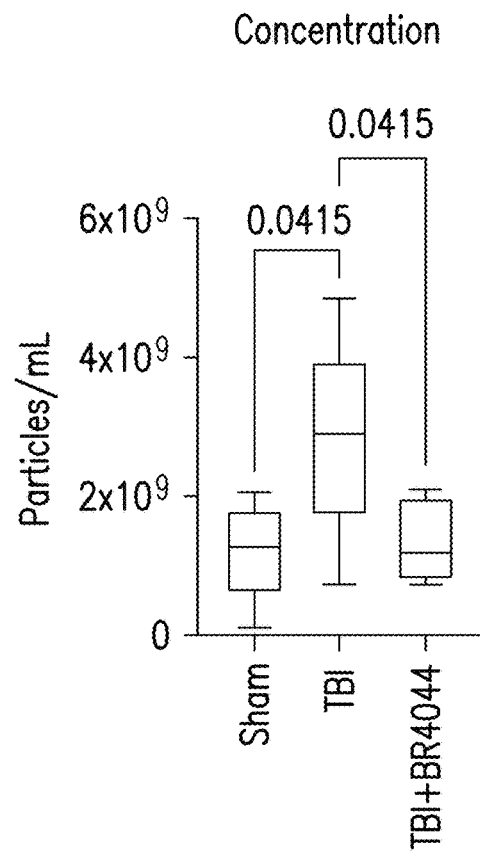
FIG.11A  FIG.11B
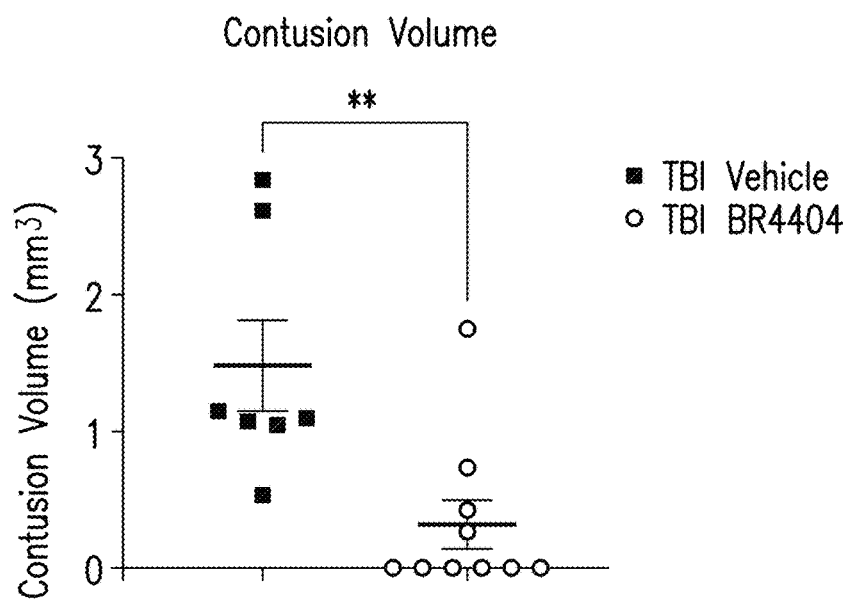
FIG.12

COMPOSITIONS AND METHODS FOR TREATING NON-HEMORRHAGIC CLOSED HEAD INJURY

RELATED APPLICATION

This application claims the benefit of priority to U.S. Provisional Application No. 63/377,834, filed Sep. 30, 2022. The contents of the above-referenced application are incorporated by reference herein in their entirety.

FIELD

Provided herein are methods of treating non-hemorrhagic closed head injury ("NHCHI"). In one embodiment, the methods involve administering 3,3'-diindolylmethane ("DIM") or a derivative thereof to a subject having or suspected of having NHCHI.

BACKGROUND

Closed-head injury ("CHI") is associated with traumatic brain injury ("TBI") in which brain damage or physiological alteration in brain function result from an external force. Open injuries, on the other hand, occur when the skull bone breaks or is penetrated, leaving the brain exposed. In CHI the skull and dura mater remain intact. CHI can be induced mechanically by direct blunt impacts, non-impact blast waves, or other deceleration injury or inertial loading. Non-hemorrhagic CHI includes concussion, also referred to as mild TBI ("mTBI"), cerebral contusion, coup-contrecoup injury, and diffuse axonal injury ("DAI") which occurs when the brain is shaken or twisted inside the skull. Second Impact Syndrome, also called recurrent TBI, is a non-hemorrhagic CHI seen when a second CHI occurs again soon after the first injury and before resolution of the initial CHI. Hemorrhagic TBIs refer to bleeding on the surface of the brain or within the brain tissue itself. Following TBI, bleeding in the space surrounding the brain is termed subarachnoid hemorrhage, while bleeding originating in the cerebral matter is termed intracerebral hemorrhage. In addition, collections of blood outside of blood vessels within the skull, or hematomas, are hemorrhagic TBIs and include epidural hematomas, subdural hematomas, and intracerebral hematomas. While hemorrhagic TBIs are treated with surgical intervention to control bleeding and evacuate blood, non-hemorrhagic CHIs lack any approved therapy. Systemic inflammatory responses to CHI remain poorly understood and are linked to both acute, ongoing brain damage immediately following the injury and chronic neurobehavioral sequelae of variable duration. Non-hemorrhagic CHIs are the most common cause of physical disability and cognitive impairment in young people and account for about 75% of an estimated 2.5 million TBIs that occur annually in the United States (Miller G F, DePadilla L, Xu L "Costs of Nonfatal Traumatic Brain Injury in the United States, 2016" Med Care. 2021 May 1; 59(5):451-455). Common behavioral and affective disorders following non-hemorrhagic CHIs include motor and cognitive deficits, as well as the early onset of agitation, aggressive behavior, and depression. CHIs may result in lifelong physical, cognitive, or psychological impairment and, thus, are of utmost concern with regards to public health. There is an unmet need for a proactive treatment to promote early functional recovery and/or prevent long-term neuropychiatric complications from CHIs. Currently there is no available drug or drug combination that is approved to reduce acute, inflammation driven CNS cellular loss following non-hemorrhagic CHIs. Nor is there any pharmacologic intervention to reduce long term behavioral changes and prevent cognitive loss following CHIs. Such a therapeutic pharmacologic compound in effective formulations would provide an important advance in the medical management of hemorrhagic and non-hemorrhagic CHI. While the sequelae of serious brain injury have been studied for many years and are relatively well characterized, the sequelae of blast-induced or concussive CHI require better understanding. Current literature suggests that persistent symptoms include a range of chronic difficulties, including neurosensory, sleep, pain, cognitive deficits, and behavioral disorders (Cifu, DX "Clinical research findings from the long-term impact of military-relevant brain injury consortium-Chronic Effects of Neurotrauma Consortium (LIMBIC-CENC) 2013-2021" Brain Inj. 2022 Apr. 16; 36(5):587-597). Dizziness, hearing loss, headaches, and neurocognitive dysfunction are frequent sequelae and, while these resolve over time in a certain portion of patients, they persist and can worsen in many patients.

The mechanical trauma of CHI induces an immediate acute-phase response ("APR") that is triggered by systemically engaging the innate immune system and amplifying the CNS injury. Extracellular Vesicle ("EV") is a general term that defines all cell-derived microparticles encapsulated in lipid bilayers, which are enriched for proteins, lipids, and nucleic acids. EVs include microvesicles (150-1,000 nm) which are blebbed from the cell membrane, while exosomes (40-150 nm) are generated via the endolysosomal pathway and stored in multivesicular bodies ("MVB") prior to release by exocytosis. Three main EV types are recognized: exosomes, microvesicles ("MVs")(including microparticles ("MPs"); and ectosomes), and apoptotic bodies (apoptotic vesicles). As part of the APR, EVs have been shown to be released from almost all cell types, including neurons and CNS endothelial cells with increased release following CNS injury (Zhao Z, Zhou Y, Tian Y, Li M, Dong J F, Zhang J. "Cellular microparticles and pathophysiology of traumatic brain injury" Protein Cell 2017, November; 8(11):801-810.). EVs have also been isolated from almost all bodily fluids, including cerebrospinal fluid (CSF) and plasma. Their release following injury disseminates information around the body, including across the blood-CNS barrier (Blood Brain Barrier (BBB)) to exert their effects both locally and systemically to distant organs, making EV's attractive candidate mediators of CNS-to-immune communication. The primary APR to CHI is followed by a secondary phase of immune-inflammatory acute damage involving further brain cell loss (within days), and a chronic (within weeks) response inducing persisting symptoms and neurobehavioral changes. To the extent that EVs provide activating surface structures which interact with leukocytes, EVs contribute to innate immune activation. EVs are recognized as important therapeutic targets to control adverse responses to traumatic injury, especially in non-hemorrhagic CHI.

EVs are primarily under study for the potential to isolate enriched fractions of EVs from stem cell populations with administration back to the patient to promote healing following various forms of injury including TBI (see, e.g., U.S. Pat. No. 11,160,834). However, leukocyte derived EVs that carry proinflammatory molecules can also propagate the inflammatory response in CHI. Following brain injury, brain cell derived microparticles including Exosomes and Microvesicles are released. Acutely released EVs are loaded with pro-inflammatory molecules which contribute to a progressive neuroinflammatory response in the injured brain, as well as, stimulating a systemic immune response.

No therapeutic agents have yet been developed or clinically evaluated which inhibit the pro-inflammatory activity of EVs released following TBI.

Diindolylmethane ("DIM"), which belongs to the class of organic compounds known as 3-alkylindoles containing an indole moiety that carries an alkyl chain at the 3-position, is known as an API with anti-cancer activity. Diindolylmethane has been used in trials studying the prevention and treatment of Breast Cancer, and Prostate Cancer, among others. As a highly insoluble crystalline solid material, DIM is difficult to formulate into drug products providing adequate oral bioavailability for needed tissue levels. With regard to CHI, DIM is an unlikely API drug candidate since it has recently been shown to have anti-thrombotic activity and prolong bleeding time (Ramakrishna K, Singh N, Krishnamurthy S "Diindolylmethane ameliorates platelet aggregation and thrombosis: In silico, in vitro, and in vivo studies" Eur. J. Pharmacol. 2022; Mar. 15; 919:174812). Anti-thrombotic activity in the clinical setting of acute CHI has the potential to convert non-hemorrhagic CHI to hemorrhagic CHI with attendant bleeding risks and potential to increase injury-related brain damage.

Thus, there is a need for a treatment for the commonly encountered medical emergency of NHCHI which reduces the response to the primary phase neurotraumatic event which is accompanied by the APR and activated release of pro-inflammatory Extracellular Microvesicles (EVs). Such a treatment may also control the secondary acute and chronic phases of immuno-inflammatory responses which are associated with neurobehavioral and neuropsychiatric sequalae.

SUMMARY

Provided herein are therapeutic drug products and methods for treating NHCHI utilizing DIM as the primary Active Pharmaceutical Ingredient ("API"). In one embodiment, treatment is directed to resolution of hyper-acute and acute symptoms and restoring Neurobehavioral Function following NHCHI. In another embodiment, drug products utilizing DIM as the primary API provide activity to diminish hyper-acute pro-inflammatory EVs and/or reduce acute and/or chronic immuno-inflammatory responses to injury associated with neurobehavioral and neuropsychiatric sequalae which follow CHI. In one embodiment, DIM is formulated into a drug product for oral administration showing rapid uptake and adequate penetration of brain tissue to control acute and chronic reactions to NHCHI. In another embodiment, intravenously administered DIM from solubilized DIM in parenterally compatible pre-concentrates suspended in sterile diluent are used in the hyper-acute and acute clinical setting of NHCHI. Intravenously administered DIM facilitates blood and brain tissue levels reaching the maximal effective dose quickly following TBI. In further embodiments, DIM is used alone or optionally in combination with a second active agent to reduce post NHCHI induced adverse behavioral changes, affective disorders, and/or loss of cognitive and/or motor function. In one embodiment, treatment is initiated as soon as possible following NHCHI, which includes mild ("mTBI") to severe concussion, blast injury due to proximity to explosions, cerebral contusion, coup-contrecoup injury, DAI, Second Impact Syndrome, and CHI associated with deceleration injury.

Without being bound by theory, timely and adequately administered DIM therapeutic drug products following NHCHI modulate acute inflammatory reactions through inhibitory control of EVs which are released from brain derived and myelocytic cellular sources. Optimization of dose, frequency of administration, and duration of DIM-based therapy is guided by assessment of clinical signs, EV numbers and related biomarkers and other TBI related biomarkers including Glial Fibrillary Acidic Protein (GFAC), according to methods well known to those of skill in the art. Pharmacological targeting of brain trauma induced EV release and innate immune activation following NHCHI using DIM and optionally a second active agent provides a method to counter the negative impact of CHI induced neuroinflammation in TBI.

BRIEF DESCRIPTION OF THE DRAWINGS

FIG. 11A-B show EV particle size (nm)(FIG. 11A) and EV concentration (particles/mL)(FIG. 11B) for serum-derived extracellular vesicles (EVs) in sham vehicle, TBI vehicle and TBI BR4404 treated rats.

FIG. 12 shows quantitative contusion volume ($mm^3$) for TBI vehicle and TBI BR4404 treated rats determined from H&E stained brain sections.

DETAILED DESCRIPTION

I. Definitions

Figure 1:
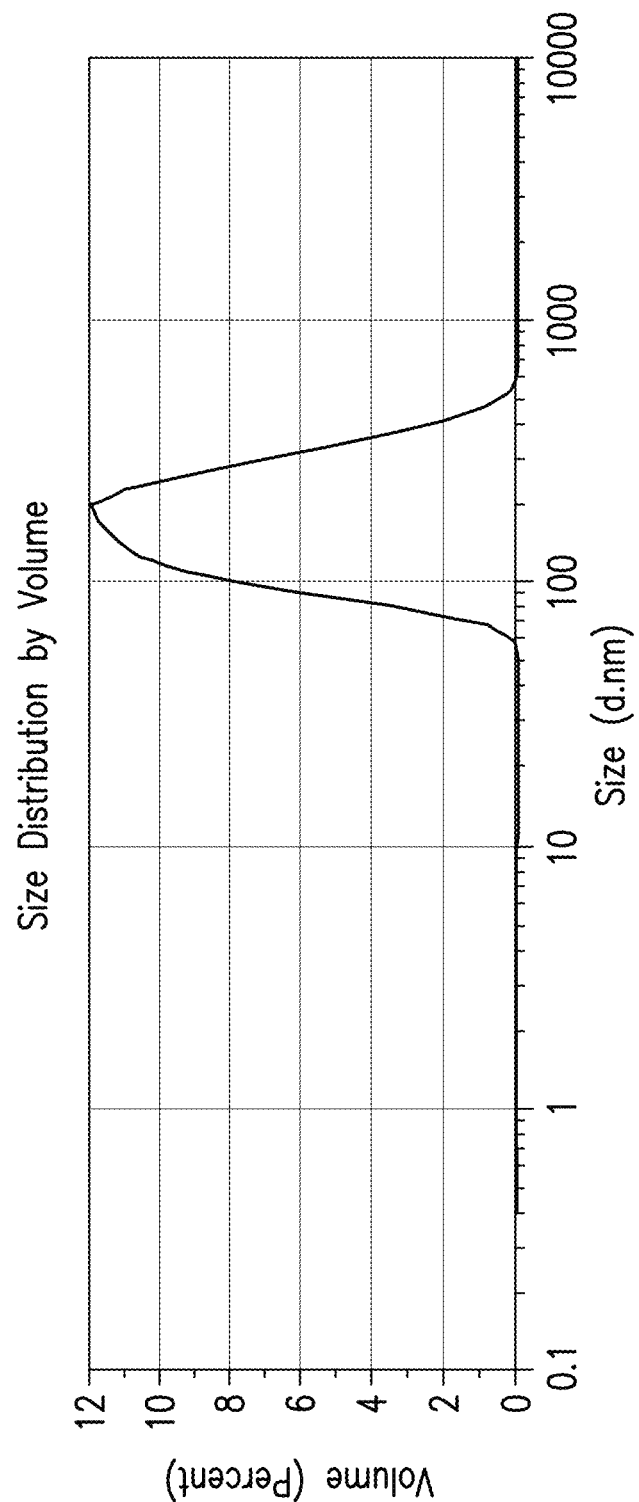
FIG. 1 shows the particle size distribution for an aripiprazole SMEDDS formulation (Example 2, Formula A).

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity demonstrated in relevant animal models, thus, encompasses therapeutic effects and pharmacokinetic behavior of such compounds, compositions, and mixtures. Biological activities can be observed in in vitro systems designed to test for such activities.

As used herein, "APR" refers to an acute-phase response to mechanical trauma of CHI that is triggered by systemically engaging the innate immune system and amplifying the CNS injury.

As used herein, "DIM" refers to 3,3'-diindolylmethane.

As used herein, a "DIM analog" refers to 1,1-bis(3,3'-indolyl)ethane ("HB-237"), 2-(indol-3-ylmethyl)-3,3'-diindolylmethane ("LTR") and/or indole-3-carbinol (1H-indol-3-ylmethanol).

As used herein, a "SMEDDS DIM" formulation refers to a self-microemulsifying drug delivery system containing DIM or a DIM analog. In one embodiment, a SMEDDS DIM formulation is a pharmaceutical composition of lipid-based excipient(s) in which DIM or a DIM analog is dissolved, providing a highly bioavailable, oral formulation. See, e.g., U.S. Pat. Nos. 9,918,965, 9,663,462, 10,441,569, 10,799,479.

As used herein, leucocytes are a type of blood cell that is made in the bone marrow and found in the blood and lymph tissue. Leukocytes are part of the body's immune system and react to acute neurotraumatic injury including CHI.

As used herein, "CHI" refers to Closed Head Injury, a category of non-penetrating Traumatic Brain Injury (TBI).

As used herein, "BBB" refers to the Blood Brain Barrier.

As used herein, "NHCHI" refers to Non-hemorrhagic Closed Head Injury (CHI).

As used herein, "EVs" refers to Extracellular Vesicles.

As used herein, "EMT" is an abbreviation for Emergency Medical Technician and is a person who is specially trained and certified to give emergency medical care including oral and intravenous medicines to patients before they reach a healthcare facility or during inter-facility transport.

As used herein, "treatment" or "treating" means any manner in which one or more of the symptoms of a disease or disorder are ameliorated or otherwise beneficially altered. Treatment also encompasses any pharmaceutical use of the compounds and compositions herein, such as use for treating NHCHI.

As used herein, amelioration of the symptoms of a particular disorder by administration of a particular compound or pharmaceutical composition refers to any lessening, whether permanent or temporary, lasting or transient that can be attributed to or associated with administration of the compound or pharmaceutical composition. Amelioration of the symptoms of a particular disorder also includes lessening the duration of illness and/or speeding the time of recovery from illness attributed to the particular disorder.

As used herein, and unless otherwise indicated, the terms "manage," "managing" and "management" encompass preventing the recurrence of the specified disease or disorder in a subject who has already suffered from the disease or disorder. The terms encompass modulating the threshold, development and/or duration of the disease or disorder, or changing the way that a subject responds to the disease or disorder.

As used herein, the $IC_{50}$ refers to an amount, concentration or dosage of a particular test compound that achieves a 50% inhibition of a maximal response in an assay that measures such response.

II. Methods of Treatment

Provided herein are methods of treating a subject having NHCHI and undergoing acute treatment by administering to the subject an effective amount of DIM or a DIM analog. In one embodiment, provided is a method of treating a subject having NHCHI which includes mild ("mTBI") to severe concussion, blast injury due to proximity to explosions, cerebral contusion, coup-contrecoup injury, Diffuse Aconal Injury (DAI), Second Impact Syndrome, and CHI associated with deceleration injury. In another embodiment, provided is a method of treating a subject having a mild concussion ("mTBI") by administering to the subject an effective amount of DIM or a DIM analog. In another embodiment, provided is a method of treating a subject having a severe concussion by administering to the subject an effective amount of DIM or a DIM analog. In another embodiment, provided is a method of treating a subject having blast injury due to proximity to explosions by administering to the subject an effective amount of DIM or a DIM analog. In another embodiment, provided is a method of treating a subject having a cerebral contusion by administering to the subject an effective amount of DIM or a DIM analog. In another embodiment, provided is a method of treating a subject having coup-contrecoup injury by administering to the subject an effective amount of DIM or a DIM analog. In another embodiment, provided is a method of treating a subject having DAI by administering to the subject an effective amount of DIM or a DIM analog. In another embodiment, provided is a method of treating a subject having Second Impact Syndrome by administering to the subject an effective amount of DIM or a DIM analog. In another embodiment, provided is a method of treating a subject having CHI associated with deceleration injury by administering to the subject an effective amount of DIM or a DIM analog.

In one embodiment, provided herein is a method of treating a subject having NHCHI and having undergone an imaging procedure which has ruled out intracranial hemorrhage by administering DIM or a DIM analog to the subject. In one embodiment, provided herein is a method of treating a subject having NHCHI who has regained consciousness following a coma and has no lateralizing signs on neurologic examination by administering DIM or a DIM analog to the subject. In one embodiment, provided herein is a method of treating a subject having NHCHI and suspected of having increased intracranial pressure for whom treatment with mannitol is contra-indicated by administering DIM or a DIM analog to the subject. In another embodiment, provided herein is a method of preventing or limiting an increase in increased intracranial pressure in a subject with NHCHI by co-administering DIM or a DIM analog in addition to mannitol or other osmotherapy agent to the subject. In another embodiment, provided herein is a method of treating a subject having NHCHI and undergoing ER physician treatment by administering DIM or a DIM analog to the subject in the pre-hospital or emergency room setting before or after an imaging study (CT or MRI) indicating a NHCHI where treatment is initiated orally or intravenously from 1 to 16 or more hours from when last seen healthy. In another embodiment, provided herein is a method of treating a subject having NHCHI with an elevated Glial Fibrillary Acidic Protein (GFAC) level or other abnormally elevated TBI related biomarker and undergoing ER physician treatment by administering DIM or a DIM analog to the subject in the pre-hospital or emergency room setting without an imaging study. In an alternative embodiment, provided herein is a method of treating a subject with hemorrhagic CHI after follow-up imaging or other evaluation has established that the intracranial bleeding has ceased or has been controlled by pro-thrombotic or surgical intervention by administering an effective amount of DIM or a DIM analog. In a further alternative embodiment, provided herein is a method of treating a subject with hemorrhagic CHI after receiving tranexamic acid or other pro-thrombotic agent to first arrest bleeding by administering to the subject an effective amount of DIM or a DIM analog.

Also provided are methods of reducing blood and CSF levels of EVs following NHCHI by contacting EVs precursor cells of the CNS, liver, spleen, and/or precursor leucocytes with DIM or a DIM analog.

In certain embodiments, DIM or a DIM analog is formulated in a SMEDDS formulation for oral administration. In other embodiments, DIM or a DIM analog is formulated for intravenous (IV) administration, optionally in the form a SMEDDS pre-concentrate for dilution and IV administration. In a further embodiment, DIM is formulated for administration directly into the cerebrospinal fluid (CSF) by lumbar puncture or via a sub-arachnoid catheter.

In one embodiment, the treatment methods provided herein are directed to resolution of hyper-acute and/or acute symptoms and/or restoring neurobehavioral function following NHCHI. In another embodiment, DIM is used alone and optionally in combination with a second active agent to reduce post NHCHI induced adverse behavioral change, affective disorders and/or loss of cognitive and/or motor function. In one embodiment, treatment is initiated as soon as possible following NHCHI, which includes but is not limited to mild ("mTBI") to severe concussion, blast injury due to proximity to explosions, cerebral contusion, coup-contrecoup injury, DAI, Second Impact Syndrome, and CHI associated with deceleration injury.

Without being bound by theory, timely and adequately administered DIM therapeutic drug products following NHCHI modulate acute inflammatory reactions through inhibitory control on the APR and EV release from brain derived and myelocytic sources. Optimization of dose, frequency of administration, route of administration, and duration of DIM-based therapy is guided by assessment of symptoms, repeated neurologic examination, API blood levels, and determinations of EV related biomarkers, as is well known to one of skill in the art.

In certain embodiments, the methods provided herein exhibit one or more of the following improvements over existing therapy by using DIM in treatment for NHCHI:

a) Improve the success rate for early resolution of acute symptoms of NHCHI which include stupor and coma, confusion, dizziness, hearing loss, headaches, and loss of balance.
b) Improve the functional outcome of NHCHI patients in the secondary phase of NHCHI who experience motor and cognitive deficits, agitation, delirium, aggressive behavior, and depression.
c) Improve the outcome of adjunctive medical therapy for CHI which include cognitive and behavioral therapy.
d) Advance the pre-hospital medical management of CHI with an orally administered agent.
e) Provide an IV agent for use in severe NHCHI patients not able to take oral medications due to additional non-CNS injuries and/or reduced level of consciousness.

The dosage and administration of pharmaceutical compositions of DIM or a DIM analog in the clinical setting of NHCHI includes oral DIM compositions for conscious patients and intravenous DIM compositions for stuporous or sedated patients. For conscious patients with symptoms of NHCHI, oral administration should be as soon as possible after CHI. In one embodiment, the composition and dosage is a SMEDDS DIM formulation providing 200-500 mg DIM per oral administration in adults, repeated after 4-8 hours three times and thereafter every 12 hours for 3-5 days. For NHCHI patients who are stuporous or sedated, intravenous (IV) administration of DIM is from a micro-suspension of DIM. In one embodiment, the dosage of IV DIM is from 50-200 mg DIM administered with a 30-minute infusion, repeated after 4-8 hours three times and thereafter every 12 hours for up to 3-5 days. In other embodiments, IV or direct to CSF compositions of DIM are administered when used in conjunction with mannitol.

III. Combination Therapy with a Second Active Agent

The methods provided herein utilizing DIM or a DIM analog can also be combined or used in combination with other therapeutic agents useful in the treatment of NHCHI.

In one embodiment, provided herein is a method of treating, preventing, or managing NHCHI, comprising administering to a subject DIM or a DIM analog in combination with one or more second active agents.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of DIM or a DIM analog and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease or disorder being treated.

The route of administration of DIM or a DIM analog is independent of the route of administration of a second therapy. In one embodiment, DIM or a DIM analog is administered orally. In another embodiment, DIM or a DIM analog is administered intravenously. Thus, in accordance with these embodiments, DIM or a DIM analog is administered orally or intravenously, and the second therapy can be administered orally, parenterally, intraperitoneally, intravenously, intraarterially, intramuscularly, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, DIM or a DIM analog and a second therapy are administered by the same mode of administration, orally or by IV. In another embodiment, DIM or a DIM analog is administered by one mode of administration, e.g., by IV, whereas the second agent is administered by another mode of administration, e.g., orally.

In one embodiment, the second active agent is administered intramuscularly, such as with aripiprazole, or sublingually and once or twice daily in an amount of from about 1 to about 1000 mg, from about 1 to about 500 mg, from about 1 to about 350 mg, from about 1 to about 50 mg, or from about 2 to about 30 mg. The specific amount of the second active agent will depend on the specific agent used, the severity and stage of disease being treated, and the amount of DIM or a DIM analog and any optional additional active agents concurrently administered to the subject.

One or more second active ingredients or agents can be used together with DIM or a DIM analog in the methods and compositions provided herein. Second active agents can be large molecules (e.g., proteins) including mono-clonal antibodies like IC-100 or small molecules (e.g., synthetic inorganic, organometallic, or organic molecules).

In one embodiment, DIM or a DIM analog can be administered in an amount ranging from about 0.1 to about 900 mg, from about 25 to about 300 mg, or from about 25 to about 400 mg orally up to 3-4 times daily alone, or in combination with a second active agent, prior to, during, or after the first dose of the second active agent.

In another embodiment, in comatose or stuporous NHCHI patients, DIM or a DIM analog is delivered in a SMEDDS excipient formulation in liquid filled capsules containing from 25-100 mg DIM or a DIM analog administered to the patient through a nasogastric tube.

In another embodiment, DIM or a DIM analog is delivered in a SMEDDS excipient formulation in liquid filled capsules which contain DIM or a DIM analog and a second active agent selected from metformin, melatonin, aripiprazole (ABILIFY®), brexpiprazole (REXULTI®), clozapine (CLOZARIL®), risperidone (RISPERDAL®), raloxifene, olanzapine (ZYPREXA®), quetiapine (Seroquel, SEROQUEL XR®), lumateperone (CAPLYTA®)m ziprasidone (GEODON®), paliperidone (INVEGA®, INVEGA SUSTENNA®, INVEGA TRINZA®), the active metabolite of risperidone, asenapine (SAPHRIS®), iloperidone (FANAPT®) and lurasidone (LATUDA®), quetiapine, lithium amantadine, chloroquine, hydroxychloroquine, p.o. sodium selenite, or I.V. SELENASE® (sodium selenite pentahydrate) 100 micrograms, solution for injection (50 micrograms/mL), selenious acid injection, or a combination thereof.

Additional second active compounds to be used with DIM or a DIM analog include GW4869, a selective, noncompetitive nSMase2 inhibitor, altenusin, a nonsteroidal fungal metabolite with broad nSMase inhibitor activity, manumycin A, a naturally occurring nSMase inhibitor, scyphostatin, cambinol, and 2,6-dimethoxy-4-(5-phenyl-4-thiophen-2-yl-1H-imidazol-2-yl)phenol (DPTIP), Tanshinone IIA sodium sulfonate (TSN-SS), SB332235, a highly selective antagonist of chemokine receptor 2 (CXCR2), IC-100, a monoclonal antibody targeting ASC, VX765, an orally-absorbed small molecule pro-drug of VRT-043198 and selective inhibitor of Caspase-1, and MCC950, a small molecule targeting NLRP3. In another embodiment, DIM or a DIM analog is delivered in a SMEDDS excipient formulation in liquid filled capsules which contain DIM or a DIM analog and a second active compound selected from aripiprazole, brexipiprazole and melatonin.

In a further embodiment, DIM or a DIM analog is delivered in combination with a second active compound which includes omega 3 Fatty Acids, tranexamic acid, complement cascade inhibitors, intrinsic or extrinsic coagulation factor inhibitors, high mobility group box 1 protein (HMBP1) inhibitors, inhibitors of BRD4 overexpression including glycyrrhizic acid, glycyrrhizin and diammonium glycyrrhizinate (DG), all-trans retinoic acid or Von Willebrand factor (VFW) inhibitors. Complement cascade inhibitors include the small molecule drugs CCX168 (TAVNEOS® (avacopan), ChemoCentryx), ACH145951 (Achillion), and LPN023 (iptacopan, Novartis). Coagulation Factor inhibitors include Factor XII inhibitors and Factor XIa inhibitors ((2S,3R)-3-([2-Aminopyridin-4-yl]methyl)-1-([{1R}-1-cyclohexylethyl] carbamoyl)-4-oxoazetidine-2-carboxylic acid (EP-7041), and asundexian (4-[[(2S)-2-[4-[5-chloro-2-[4-(trifluoromethyptriazol-1-yl]phenyl]-5-methoxy-2-oxopyridin-1-yl]butanoyl]amino]-2- fluorobenzamide, BAY 2433334).

In another embodiment, DIM or a DIM analog is delivered in a SMEDDS excipient formulation in liquid filled capsules which contain DIM or a DIM analog co-formulated with a second active compound selected from glycyrrhizin, atypical antipsychotic drugs, including aripiprazole or brezpiprazole, and/or metformin and/or melatonin and/or hydroxychloroquine.

In another embodiment, further DIM centered therapy for CHI includes administration of a DIM therapeutic drug product in combination with a second active agent known to modify the cellular loss from acute injury and/or curtail the delayed brain damage associated with adverse neurobehavioral outcome following CHI. In one embodiment, such combined administration of a second active agent in addition to DIM is parenteral and includes IV or subcutaneous administration of mono-clonal antibodies such as IC-100. In another embodiment, the combined administration is oral and includes co-administration of atypical antipsychotics, like aripiprazole and brexpiprazole, metformin, melatonin, and hydroxychloroquine. In a further embodiment, the DIM and aripirazole can be co-formulated in a single SMEDD formulation, encapsulated in a single capsule, and co-administered in a fixed dose combined drug product (see, e.g., Example 2).

In another embodiment, provided is a composition containing DIM and an atypical anti-psychotic drug. In another embodiment, provided is a composition containing DIM, an atypical anti-psychotic drug and a pharmaceutically acceptable carrier. In one embodiment, the atypical anti-psychotic drug is aripiprazole or brexpiprazole. In another embodiment, the atypical anti-psychotic drug is aripiprazole. In one embodiment, the composition containing DIM and an anti-psychotic drug is formulated for intravenous administration. In another embodiment, the composition containing DIM and an anti-psychotic drug is formulated for oral administration. In one embodiment, the composition containing DIM and an anti-psychotic drug is a self-micro-emulsifying drug delivery (SMEDD) formulation. In one embodiment, the composition containing DIM and an anti-psychotic drug is a SMEDD formulation containing 3,3'-diindolylmethane, aripiprazole, caprylocaproyl polyoxyl-8 glycerides, lauroyl polyoxyl 32 glycerides, polyethylene-polypropylene glycol, oleoyl polyoxyl-6 glycerides and phosphatidyl choline.

IV. DIM or a DIM Analog for Use in Compositions and Methods

The methods provided herein include use of 3,3'-diindolylmethane ("DIM"). In one embodiment, DIM is provided in a self micro-emulsifying drug delivery (SMEDDS) formulation. Such SMEDDS DIM formulations are known in the art, including those described herein in Examples 1-4, and disclosed in U.S. Pat. Nos. 9,918,965, 9,663,462, 10,441,569, 10,799,479.

In other embodiments, the methods provided herein include use of a DIM analog. DIM analogs include:

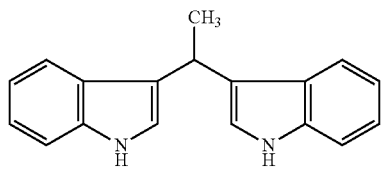 [SMILES: CC(c1c[nH]c2ccccc12)c1c[nH]c2ccccc12]

(i.e., 1,1-bis(3,3'-indolypethane_("HB-237"));

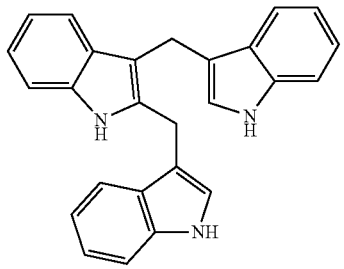 [SMILES: c1ccc2c(Cc3[nH]c4ccccc4c3Cc3c[nH]c4ccccc34)c[nH]c2c1]

(i.e., 2-(indol-3-ylmethyl)-3,3'-diindolylmethane ("LTR")); and

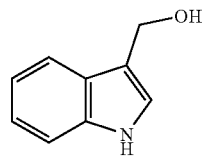 [SMILES: OCc1c[nH]c2ccccc12]

(i.e., indole-3-carbinol or 1H-indol-3-ylmethanol). It has been shown that indole-3-carbinol converts to DIM and LTR in vivo. See, e.g., Anderton et al., Clin. Cancer Res. 10:5233-5241 (2004).

IV. Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically, the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and then extrapolated therefrom for dosages for humans. In some embodiments, the active compound is administered in a method to achieve a therapeutically effective concentration of the drug. In some embodiments, a companion diagnostic (see, e.g., Olsen D and Jorgensen J T, Front. Oncol., 2014

May 16, 4:105, doi:10.3389/fonC.2014.00105) is used to determine the therapeutic concentration and safety profile of the active compound in specific subjects or subject populations.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerin, propylene glycol, dimethyl acetamide or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium croscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmacopeia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

A. Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, crospovidone, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene lauryl ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil in-water or water in oil. In some embodiments, the suspension is a suspension of microparticles or nanoparticles. In some embodiments, the emulsion is an emulsion of microparticles or nanoparticles.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Orally administered DIM therapeutic drug products require adequate bioavailability as exemplified by Self-Micro-Emulsifying-Drug-Delivery (SMEDD) formulations such as those described in Example 1, but not limited to this formulation or absorption-enhancing technology. Alternatively, the DIM therapeutic drug products can be administered intravenously in the pre-hospital or acute care setting utilizing a SMEDD-based intravenous DIM formulation, including but not limited to those described in Example 4.

B. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. In some embodiments, the suspension is a suspension of microparticles or nanoparticles. In some embodiments, the emulsion is an emulsion of microparticles or nanoparticles. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, intrathecal, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile premix formulations to be diluted forming sterile emulsions just prior to use. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof. Further, carriers that specifically solubilize DIM-related indoles are described in Example 4.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically, a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The second active agent and/or DIM or a DIM analog may be suspended in micronized or other suitable form or may be derivatized to produce a more soluble active product or to produce a prodrug. The form of the resulting mixture depends upon a number of factors, including the intended mode of administration and the solubility of the second active agent and/or DIM or a DIM analog in the selected carrier or vehicle. The effective concentration is sufficient for ameliorating the symptoms of the condition and may be empirically determined.

In another embodiment, provided for use in the methods provided herein are IV formulations of DIM or a DIM analog containing one or more of anhydrous ethanol, polyoxyl castor oil, phosphatidyl choline, oleoyl polyoxyl-6 glycerides and poly(ethylene glycol)-block-poly(propylene glycol)-block-poly(ethylene glycol) copolymer. In another embodiment, the IV formulations contain DIM. In another embodiment, the IV formulations contain 10% DIM, 43% anhydrous ethanol, 19% polyoxyl castor oil, 8% phosphatidyl choline, 9% oleoyl polyoxyl-6 glycerides and 11% poly(ethylene glycol)-block-poly(propylene glycol)-block-poly(ethylene glycol) copolymer. In further embodiments, the polyoxyl castor oil is BASF KOLLIPHOR® EL. In another embodiment, the oleoyl polyoxyl-6 glycerides are Gattefosse LABRAFIL® M1944 CS. In another embodiment, the poly(ethylene glycol)-block-poly(propylene glycol)-block-poly(ethylene glycol) copolymer is BASF Poloxamer 188. In another embodiment, the IV formulations contain 10% 3,3'-diindolylmethane, 43% anhydrous ethanol, 19% BASF KOLLIPHOR® EL, 8% Phosphatidyl Choline, 9% Gattefosse LABRAFIL® M1944 CS, and 11% BASF Poloxamer 188.

In another embodiment, provided are IV formulations of DIM or a DIM analog containing one or more of anhydrous ethanol, medium chain triglycerides, phosphatidyl choline, polyoxyl 15 hydroxystearate, and one or more poly(ethylene glycol)-block-poly(propylene glycol)-block-poly(ethylene glycol) copolymers. In another embodiment, the IV formulations contain DIM. In another embodiment, the IV formulations contain 2% DIM, 45% anhydrous ethanol, 10% medium chain triglycerides, 8% phosphatidyl choline, 15% polyoxyl 15 hydroxystearate, and 20% of one or more poly(ethylene glycol)-block-poly(propylene glycol)-block-poly(ethylene glycol) copolymers. In another embodiment, the medium chain triglycerides are Gattefosse WL 1349. In another embodiment, the polyoxyl 15 hydroxystearate is BASF HS-15. In another embodiment, the one or more poly(ethylene glycol)-block-poly(propylene glycol)-block-poly(ethylene glycol) copolymers are poloxamer 188 and/or poloxamer 407. In another embodiment, the IV formulations contain 2% DIM, 45% anhydrous ethanol, 10% Gattefosse WL 1349, 8% phosphatidyl choline, 15% BASF HS-15, 8% poloxamer 188 and 12% poloxamer 407.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

D. Compositions for Other Routes of Administration

Other routes of administration, such as topical application, transdermal patches, intrathecal administration and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

In one embodiment, DIM or a DIM analog is provided in a parenteral microdispersion for intra-arterial administration. In another embodiment, DIM or a DIM analog is provided in a sterile lyophilized powder for dilution and intrathecal administration.

F. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased subject compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

G. Targeted Formulations

The compounds provided herein, or pharmaceutically acceptable salts thereof, may also be formulated to be targeted to a particular tissue, receptor, intracellular or extracellular structure, or other tissue of the body of the subject to be treated, including liposome-, resealed erythrocyte-, and antibody-based delivery systems using humanized mono-clonal antibodies. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, the antibody-based delivery system is an antibody-drug conjugate ("ADC"), e.g., as described in Hamilton G S, Biologicals, 2015 September, 43(5):318-32; Kim E G and Kim K M, Biomol. Ther. (Seoul), 2015 November, 23(6):493-509; and Peters C and Brown S, Biosci. Rep., 2015 Jun. 12, 35(4) pii:e00225, each of which is incorporated herein by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

H. Articles of Manufacture

The second active agent and/or DIM or a DIM analog can be packaged as articles of manufacture containing packaging material, a second active agent and/or DIM or a DIM analog thereof provided herein, which is used for treatment, prevention or amelioration of one or more symptoms or progression of a disease or disorder disclosed herein, and a label that indicates that the second active agent and/or DIM or a DIM analog is used for treatment, prevention or amelioration of one or more symptoms or progression of a disease or disorder disclosed herein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In certain embodiments, provided herein also are kits which, when used by the medical practitioner, can simplify the administration of appropriate amounts of active ingredients to a subject. In certain embodiments, the kit provided herein includes a container and a dosage form of a second active agent and/or DIM or a DIM analog provided herein.

Embodiments of kits providing DIM or a DIM analog and a second active agent for oral use in the setting of NHCHI include the following second active agents administered as soon as possible after the onset of symptoms:

| Second Active Agent | Manufacturer | Dose Range |
| --- | --- | --- |
| Aripiprazole | Generic | 2.5-20 mg p.o. daily |
| Brexpiprazole | Otsuka | 0.25 to 5 p.o. daily |
| Metformin | Generic | 50-200 mg p.o. B.I.D or T.I.D. |
| Tranexamic acid | Generic | Oral: 650-1000 mg p.o. T.I.D. IV: 800-1000 mg every 6 to 8 hours, equivalent to 15 mg/kg BW |
| Diammonium Glycyrrhizinate | Generic | Oral: 150-300 mg p.o. TID |
| Molecular Hydrogen dissolved to saturation in Normal Saline, D5W, or $H_2O$ | Generic | Infused IV at 0.5 to 3 Liters per 24 hrs. Oral: 500 cc P.O. T.I.D. |
| Melatonin | Generic | 2-20 mg p.o. q.h.s., B.I.D. or T.I.D. |

In certain embodiments, the kit includes a container comprising a dosage form of the second active agent and/or DIM or a DIM analog provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

V. Dosing

The second active agent and/or DIM or a DIM analog and pharmaceutical compositions provided herein may be dosed in certain therapeutically or prophylactically effective amounts, certain time intervals, certain dosage forms, and certain dosage administration methods as described below.

In certain embodiments, a therapeutically or prophylactically effective amount of the second active agent and/or DIM or a DIM analog is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the second active agent and/or DIM or a DIM analog provided herein, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the second active agent and/or DIM or a DIM analog can be administered in an amount of about 25 mg/day. In a particular embodiment, the second active agent and/or DIM or a DIM analog can be administered in an amount of about 10 mg/day. In a particular embodiment, the second active agent and/or DIM or a DIM analog can be administered in an amount of about 5 mg/day. In a particular embodiment, the second active agent and/or DIM or a DIM analog can be administered in an amount of about 4 mg/day. In a particular embodiment, the second active agent and/or DIM or a DIM analog can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The dosage and administration of pharmaceutical compositions of DIM or a DIM analog in the clinical setting of NHCHI is guided by the presenting condition of the patient and current standard of care guidelines, as is well known to those of skill in the art. For conscious patients with symptoms of NHCHI with imaging confirmation of absence of intracranial hemorrhage based on Computerized Tomography (CT) or Magnetic Resonance Imaging (MRI), oral administration is preferred as soon as possible. In one embodiment, the composition and dosage is a SMEDDS DIM formulation providing 100-500 mg DIM per oral administration, repeated after 4-8 hours three times and thereafter every 12 hours for 3-5 days. For NHCHI patients who are stuporous or sedated, intravenous (IV) administration of DIM is from a micro-suspension of DIM (e.g., Example 4). In one embodiment, the dosage of IV DIM is from 20-200 mg DIM administered with a 30-minute infusion, repeated after 4-8 hours three times and thereafter every 12 hours for up to 3-5 days.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the second active agent and/or DIM or a DIM analog administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the second active agent and/or DIM or a DIM analog administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a second active agent and/or DIM or a DIM analog provided herein, or a derivative thereof. Once steady state is reached, there are minor peaks and troughs on the time dependent curve of the plasma concentration of the compound.

In certain embodiments, the amount of the second active agent and/or DIM or a DIM analog administered is sufficient to provide a maximum plasma concentration (peak concentration) of the second active agent and/or DIM or a DIM analog, ranging from about 0.001 to about 50 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the second active agent and/or DIM or a DIM analog administered is sufficient to provide a minimum plasma concentration (trough concentration) of the second active agent and/or DIM or a DIM analog, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the second active agent and/or DIM or a DIM analog administered is sufficient to provide an area under the curve (AUC) of the second active agent and/or DIM or a DIM analog, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The methods provided herein encompass treating a patient regardless of subject's age, although some diseases or disorders are more common in certain age groups. For example, treating NHCHI in the pediatric age group (2-12 years of age) involves scaling the adult dose downward to not exceed the plasma level of DIM or second active agent associated with the maximal tolerated dose (MTD) in adult patients. Such downward scaling of the adult dose is within ability of the skilled artisan using well known techniques.

Depending on the severity of NHCHI to be treated and the subject's condition, the second active agent and/or DIM or a DIM analog provided herein, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The second active agent and/or DIM or a DIM analog provided herein, may be formulated, alone or together, in suitable dosage unit with pharmaceutically acceptable excipients, carriers, adjuvants and vehicles, appropriate for each route of administration.

In one embodiment, the second active agent and/or DIM or a DIM analog provided herein is administered orally. In another embodiment, the second active agent and/or DIM or a DIM analog provided herein is administered parenterally. In yet another embodiment, the second active agent and/or DIM or a DIM analog provided herein is administered intravenously.

The second active agent and/or DIM or a DIM analog provided herein can be delivered as a single dose such as, e.g., a single bolus injection, or oral tablets or pills; or over time, such as, e.g., continuous infusion over time or divided bolus doses over time. The second active agent and/or DIM or a DIM analog can be administered repeatedly if necessary, for example, until the subject experiences stable disease or regression, or until the subject experiences disease progression or unacceptable toxicity.

The second active agent and/or DIM or a DIM analog provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the second active agent and/or DIM or a DIM analog provided herein is administered once or more than once each day, for example, for a period of time. The term "continuous" is intended to mean that a therapeutic compound, such as the second active agent and/or DIM or a DIM analog provided herein is administered daily for an uninterrupted period of at least 10 days to 52 weeks. The term "intermittent" or "intermittently" as used herein is intended to mean stopping and starting at either regular or irregular intervals. For example, intermittent administration of the second active agent and/or DIM or a DIM analog provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the second active agent and/or DIM or a DIM analog provided herein is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the second active agent and/or DIM or a DIM analog provided herein is administered once a day. In another embodiment, the second active agent and/or DIM or a DIM analog provided herein is administered twice a day. In yet another embodiment, the second active agent and/or DIM or a DIM analog provided herein is administered three times a day. In still another embodiment, the second active agent and/or DIM or a DIM analog provided herein is administered four times a day.

In certain embodiments, the second active agent and/or DIM or a DIM analog provided herein is administered once per day from one day to six months, from one week to three months, from one week to four weeks, from one week to three weeks, or from one week to two weeks. In certain embodiments, the second active agent and/or DIM or a DIM analog provided herein is administered once per day for one week, two weeks, three weeks, or four weeks. In one embodiment, the second active agent and/or DIM or a DIM analog provided herein is administered once per day for 4 days. In one embodiment, the second active agent and/or DIM or a DIM analog provided herein is administered once per day for 5 days. In one embodiment, the second active agent and/or DIM or a DIM analog provided herein is administered once per day for 6 days. In one embodiment, the second active agent and/or DIM or a DIM analog provided herein is administered once per day for one week. In another embodiment, the second active agent and/or DIM or a DIM analog provided herein is administered once per day for two weeks. In yet another embodiment, the second active agent and/or DIM or a DIM analog provided herein is administered once per day for three weeks. In still another embodiment, the second active agent and/or DIM or a DIM analog provided herein is administered once per day for four weeks.

VI. Examples

The examples below are meant to illustrate certain embodiments provided herein, and not to limit the scope of this disclosure.

Example 1

Production of SMEDDS DIM Formulation and Placebo SMEDDS Vehicle

Method 1: The following were added to a small scintillation vial in the following order: 2.8 grams caprylocaproyl polyoxyl-8 glycerides (Gattefosse LABRASOL® ALF), 1.8 grams lauroyl polyoxyl 32 glycerides (Gattefosse GELUCIRE® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH$), 1.0 grams oleoyl polyoxyl-6 glycerides (Gattefosse LABRAFIL® M1944CS). The mixture was warmed and gently agitated to uniformity. 0.8 Grams of phosphatidyl choline (Lipoid PHOSPHOLIPON® 90G) was added to the mixture with warming to approximately 70° C. After cooling to approximately 50° C., 1.2 grams of 3,3'-diindolylmethane (BioResponse, LLC) was added with continuing agitation until the mixture was uniform.

Method 2: Production method for SMEDDS DIM Formulation:

| Ingredient | Supplier | Percentage |
|---|---|---|
| GELUCIRER 44/14 | Gattefosse | 18.0% |
| LABRASOL ® ALF | Gattefosse | 28.0% |
| Poloxamer 124 | BASF | 24.0% |
| LABRAFIL ® M1944CS | Gattefosse | 10.0% |
| PHOSPHOLIPON ® 90G | Lipoid | 8.0% |
| 3,3'-diindoly lmethane | BioResponse, LLC | 12.0% |
| Total | | 100.0% |

Containers of GELUCIRE® 44/14 and poloxamer 124 were placed in an oven or appropriate warming bath set at approximately 50° C. An appropriately sized container was equipped with overhead agitator and thermometer. Either a jacketed container was used or a hot plate was used to be able to heat the container. The GELUCIRE®, the poloxamer, the LABRASOL® ALF, and the LABRAFIL® M1944 CS were each added sequentially in this order to the container with stirring. The mixture was homogeneous. The mixture was heated to range of 50 to 60° C. with continued stirring. The granular PHOSPHOLIPON® 90G was stored refrigerated. It was removed from the refrigeration and allowed to come to room temperature before opening the container. The amount was weighed and added to the stirring container. Agitation was increased to appropriate speed so as not to entrain air. The mixture was stirred to uniformity which may take several hours at temperature. The mixture was allowed to cool to approximately 40 to 45° C. and the 3,3'-diindolylmethane was weighed and added with stirring. The container was covered in foil to keep out of direct light. The mixture was uniform within 30 minutes. The mixture can be stored in appropriate amber glass containers out of direct light.

Method 3: Production of Placebo SMEDDS vehicle

| Ingredient | Supplier | Percentage |
|---|---|---|
| GELUCIRER 44/14 | Gattefosse | 20.45% |
| LABRASOL ® ALF | Gattefosse | 31.82% |
| Poloxamer 124 | BASF | 27.27% |
| LABRAFIL ® M1944CS | Gattefosse | 11.36% |
| PHOSPHOLIPON ® 90G | Lipoid | 9.10% |
| Total | | 100.0% |

The placebo was made the same way as in Method 2 above except for exclusion of the addition of DIM. The placebo mixture does not need to be covered with foil.

Example 2

Co-Formulation of DIM and Atypical Anti-Psychotics in a Single Oral SMEDDS Drug Product More effective early therapy of NHCHI is anticipated using the combination of DIM and second active atypical anti-psychotic drugs, aripiprazole or brexpiprazole (REXULTI®). Prototype drug product development was undertaken to prove that co-formulation of API DIM and API aripiprazole was feasible in the same SMEDDS vehicle excipients needed to promote absorption of DIM. The combination, co-formulated products would include the pharmaceutical formulation of diindolylmethane (DIM) of Example 1, supra, and the schizophrenia medication, aripiprazole or brexpiprazole. In order to see if this would be possible, a series of experiments were initiated to determine the solubility of the aripiprazole in the formulation of Example 1.

Sample Preparation of SMEDDS DIM—10 grams of SMEDDS DIM was prepared by mixing the following:
- 1.8 grams of Gelucire 44-14 (Gattefosse)
- 2.8 grams Labrasol ALF (Gattefosse)
- 1.0 grams Labrasol M1944CS (Gattefosse)
- 2.4 grams Poloxamer 124 (BASF)
- 1.2 grams Diindolylmethane (BioResponse)
- 0.8 grams Phospholipon 90 (American Lecithin)

The above was heated to approximately 60 degrees C. and stirred to uniformity.

The following was weighed into small vials in the following order to make the above mixture: 2.8 grams caprylocaproyl polyoxyl-8 glycerides (Gattefosse LABRASOL® ALF), 1.8 grams lauroyl polyoxyl 32 glycerides (Gattefosse GELUCIRE® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH$), 0.8 grams oleoyl polyoxyl-6 glycerides (Gattefosse LABRAFIL® M1944CS). The mixture was warmed and gently agitated to uniformity. 0.8 Grams of phosphatidyl choline (Lipoid PHOSPHOLIPON® 90G) was added to the mixture with warming to approximately 80° C. After cooling to approximately 50° C., 1.2 grams of 3,3'-diindolylmethane (BioResponse, LLC) was added with continuing agitation until the mixture was uniform. In a separate small scintillation vial, a 100:1 dilution of aripiprazole was prepared by adding 100 mg of aripiprazole to 9.90 grams of oleoyl polyoxyl-6 glycerides (Gattefosse LABRAFIL® M1944CS). 200 mg of this dilution was added to the formulation representing 2.0 mg of aripiprazole and the mixture stirred to uniformity.

10 mg aripiprazole, 0.81 grams SMEDDS DIM=1.2%

10 mg aripiprazole, 0.49 grams SMEDDS DIM=2.0%

25 mg aripiprazole, 0.475 grams SMEDDS DIM=5.0%

50 mg aripiprazole, 0.45 grams SMEDDS DIM=10%

Results: The mixtures were agitated and stored overnight. After warming to fluidity at about 35 degrees C., it was clear that the 1.2% formulation showed no suspension, that all had dissolved, the 2.0% solids had not quite dissolved with probably less than 2 mg still in suspension and the 5% and 10% suspensions showed white solids clearly present.

Conclusion of co-dissolution shows that a dose of up to 10 mg aripiprazole can be dissolved in a standard dose of 100 mg of DIM contained in 825 mg of the SMEDDS DIM. The solubility of the aripiprazole in the SMEDDS DIM formulation is in the range of approximately 1.5%.

The prototype co-formulation of DIM and aripiprazole was further analyzed with dispersion studies to determine if there might be any synergism in SMEDDS functional performance in generating the smallest of nano-dispersions. The following formulations were prepared for comparison to the SMEDDS DIM formulation made with 12% DIM (Example 1). Previously run samples of a similar formula with just DIM at 12% active gave a value of 145 nm for the Z-average.

| Ingredient | Supplier | Formula A (Only Aripiprazole) | | Formula B (DIM plus Aripiprazole) | |
|---|---|---|---|---|---|
| | | gms | % wt | gms | % wt |
| Gelucire 44/14 | Gattefosse | 2.1 | 21 | 2.0 | 20 |
| Labrasol ALF | Gattefosse | 3.2 | 32 | 3.0 | 30 |
| Poloxamer 124 | BASF | 2.6 | 26 | 2.5 | 25 |
| Labrafil M1944CS | Gattefosse | 1.1 | 11 | 1.1 | 11 |
| Phopholipon 90 | Lipon | 0.8 | 8 | 0.8 | 8 |
| Aripiprazole | Sigma Aldrich | 0.2 | 2 | 0.1 | 1 |
| 3,3'-Diindolylmethane | BioResponse | | | 0.5 | 5 |
| Evaluation of Particle Size by Malvern Zetasizer | | Z-Average (nm) 162.4 (See FIG. 1) | | Z-Average (nm) 88.2 (See FIG. 2) | |

The formulations above were prepared as described below.

Production method for Formula A and B tested for particular dispersions:

Containers of GELUCIRE 44/14 and Poloxamer 124 were placed in an oven or an appropriate warming bath set at approximately 50° C. An appropriately sized container was equipped with overhead agitator and thermometer. Either a jacketed container was used or a hot plate was used to be able to heat the container. The GELUCIRE44/14, the Poloxamer 124, the LABRASOL ALF, and the LABRAFIL M1944 CS were each added sequentially in this order to the container with stirring. The mixture was homogeneous. The mixture was heated to range of 50 to 60° C. with continued stirring. The granular PHOSPHOLIPON® 90G had been stored refrigerated. It was removed from the refrigeration and allowed to come to room temperature before opening the container. The amount was weighed and added to the stirring container. Agitation was increased to appropriate speed so as not to entrain air. The mixture was stirred to uniformity which may take several hours at temperature. The mixture was allowed to cool to approximately 40 to 45° C. and the 3,3'-diindolylmethane was weighed and added with stirring along with the aripiprazole as appropriate. The container was covered in foil to keep out of direct light. The amber-colored clear mixtures are uniform within 30 minutes. The mixtures can be stored in appropriate amber glass containers out of direct light.

Particle size measurements were taken of the dispersions in water using a Malvern Zetasizer nano ZS by Particle Technology Labs in Downers Grove, IL 60515. Intensity weighted Z average are reported (See Table, above)

Formula A Z-Average (nm)=162.4

Formula B Z-Average (nm)=88.8

SMEDDS DIM (Example 1) Z-Average (nm)=145

Figure 2:
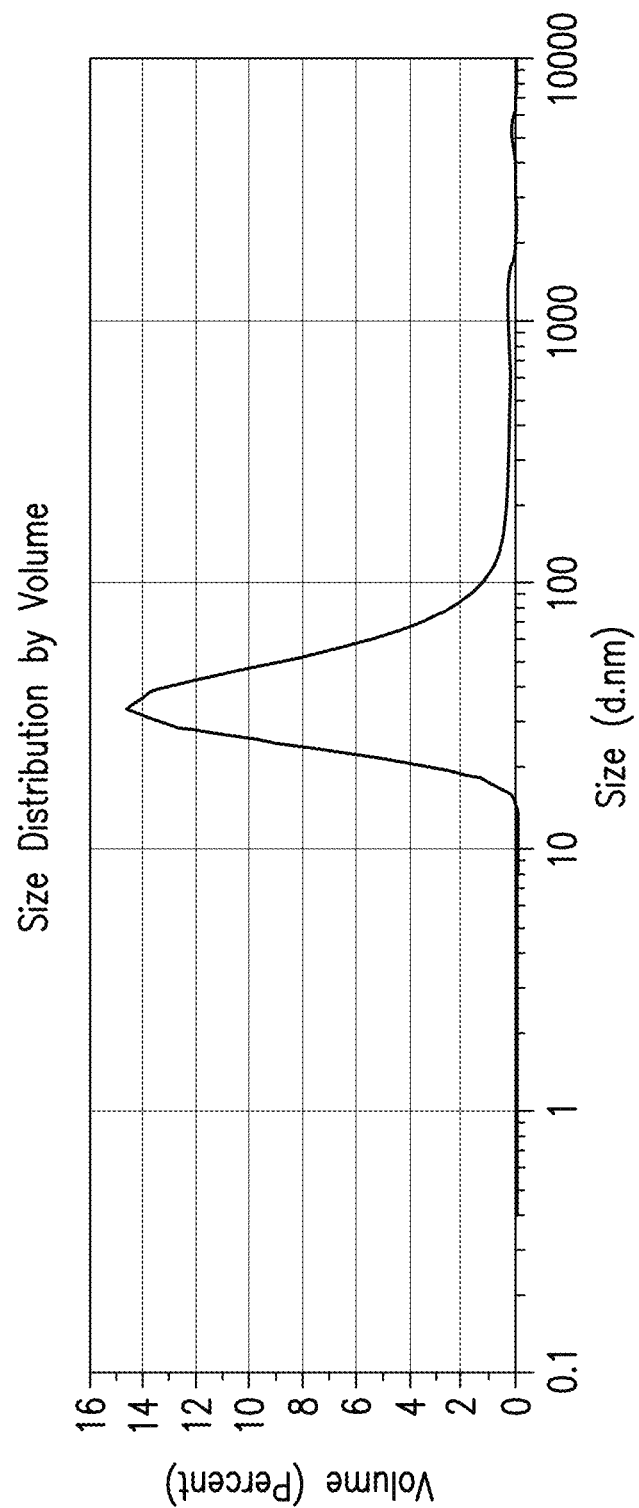
FIG. 2 shows the particle size distribution for an aripiprazole/DIM SMEDDS formulation (Example 2, Formula B).

The intensity weighted size distribution graphs for each of Formula A and Formula B are shown in the attached figures (See FIG. 1 (Formula A (Only Aripiprazole)) and FIG. 2 (Formula B (DIM plus aripiprazole)).

Conclusions: The above data shows that the Formula B does show evidence that a mixture of aripiprazole and DIM provides for an excellent nano-dispersion in water. The smaller particle size seen with the combination, co-formulated product (Formula B) is a surprising finding and provides evidence of a synergism when both actives are present together to producing an even smaller particle size dispersion than in the DIM alone at 12% when DIM is present as a single ingredient. The reduced size of particles in Formula B (88.8 nm) compared to previously established particle size from SMEDDS DIM at 12% (Z average=145 nm) indicates that Formula B will promote more rapid uptake of DIM in the gastrointestinal system. These results show an unanticipated advantage of the Formula B combined formulation over co-administering SMEDDS DIM (Example 1) and aripiprazole in separate capsule/tablets.

The projected clinical use of a 1000 mg capsule of Formula B providing 50 mg DIM and 5 mg aripiprazole once or twice daily is appropriate for the treatment of NHCHI during the acute and chronic phase when lower than typical dosing of aripiprazole is anticipated. Alternatively, brexpiprazole can replace aripiprazole in Formula B at a lower dose per capsule in the range of 0.25 to 1 mg per capsule.

Example 3

Manufacture of an Alternative SMEDDS DIM Formulation with Caproyl-90

In a manner similar to Examples 1 and 2, the following components were used to form a SMEDDS DIM formulation: 2.8 grams caprylocaproyl polyoxyl-8 glycerides (Gattefosse LABRASOL® ALF), 1.8 grams lauroyl polyoxyl 32 glycerides (Gattefosse Gelucire® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH$), 1.0 grams oleoyl polyoxyl-6 glycerides (Gattefosse LABRAFIL® M1944CS), 0.4 grams of phosphatidyl choline (Lipoid PHOSPHOLIPON® 90G), 0.4 g caproyl-90 (propylene glycol mono- and diesters of caprylic acid, >90% monoester).

Example 4

Development of a Premix Formulation of 3,3'-Diindolylmethane (DIM) for Suspension in Physiologic Diluent and Intravenous Administration—an IV DIM Drug Product Hospital based management of severe NHCHI is associated with stupor, coma, and diminished levels of consciousness combined with need for rigid cervical spine fixation in cases where C-spine injury may accompany CHI. In these cases, patients require "nothing by mouth (NPO)" status. For these reasons a DIM-specific intravenous formulation was developed to provide for efficient NHCHI therapy in hospitalized patients. The present formulation allows for ease of administration and for achieving the highest possible plasma and tissue levels of DIM soon following NHCHI. Typical dosage will be from 25-200 mg DIM given IV every 8 hours for up to 5 consecutive days.

After testing several formulation prototypes using a subset of DIM compatible excipients with a history of use in parenteral drug products, the following mixture was developed for the IV DIM Premix drug product. The prototype was produced, tested for stability of typical pre-administration dispersion, and made ready for further development for clinical trial application as an intravenous dosage form for DIM.

Development and Use of a Parenteral, DIM Premix Drug Product

Introduction: The following describes the development of a concentrated, IV premix drug product which provides a shelf stable DIM drug product for intravenous use. The drug product is ready for dilution into a nano-scale suspension and for immediate intravenous administration by pre-hospital Emergency Medical Technicians (EMT's), by in-hospital Emergency Departments, and by Radiologists evaluating NHCHI patients. Such a drug product advances current protocols for use during pre-hospital and inter-hospital transport of serious NHCHI patients. A drug formulation yielding a dispersion of nano-scale particles of DIM for intravenous use fills an important unmet need for early initiation of therapy and to improve the outcome of NHCHI treatment.

The extremely low solubility of DIM in both oil and water combined with regulatory restrictions on the number of acceptable excipients for parenteral administration make development of a functional premix for API DIM a formidable formulation challenge. Safety concerns related to parenteral administration of lipid-based excipients, surfactants and polymers put limitations on formulation development for a DIM-related parenteral premix. Working within these constraints, DIM compatible excipients with appropriate solubilizing activity and safety record were determined based on physicochemical characteristics and history of prior regulatory approval (Table 1). These formulation excipient components are clearly different than those discovered to provide Self Micro-Emulsify Drug Delivery (SMEDD) formulations for oral administration of DIM-related indoles as specified in U.S. Pat. Nos. 9,918,965, 10,441,569, and 10,779,479. The present premix formulations were assessed for ability to dissolve DIM or DIM derivatives. Following this, the premix formulations were tested for dispersion formation following dilution in physiologic aqueous media to emulate clinical use. Formulations 1-10 (Table 2) were observed following spontaneous dispersion formation and the stability of the resulting nano-scale dispersions was assessed.

TABLE 1

Excipient Materials Selected as Candidates for Parenteral DIM Formulations

| Excipient | Tradename | Manufacturer | Physical Form |
|---|---|---|---|
| Diethylene glycol mono-ethyl ether | Transcutol | Gattefosse | Liquid |
| Medium chain triglycerides | Labrafac WL1349 | Gattefosse | Liquid |
| Oleoyl polyoxyl-6 glycerides | Gattefosse Labrafil M1944CS | Gattefosse | Liquid |
| Phosphatidyl choline | PhosphoLipon 90G | Lipoid | Solid |

TABLE 1-continued

Excipient Materials Selected as Candidates for Parenteral DIM Formulations

| Excipient | Tradename | Manufacturer | Physical Form |
|---|---|---|---|
| Polyoxyl-15 hydroxystearate | Kolliphor HS-15 | BASF | Semi-solid |
| Poloxamer 188 | Kolliphor P188 | BASF | Solid |
| Poloxamer 407 | Kolliphor P407 | BASF | Solid |
| Diindolylmethane (DIM) | Pharmaceutical DIM | BioResponse | Crystalline Solid |
| 95% Ethanol | Everclear | Sigma Aldrich | Liquid |
| Sodium chloride | | Sigma Aldrich | Solid |

Manufacture of Anhydrous DIM Premix Formulations

The following premix prototypes were prepared at a quantity of 10 grams each (Table 2). Transcutol (Gattefosse, FR) was included as a candidate excipient although it is not currently used in approved parenteral products. Transcutol has been tested in Europe for parenteral use and considered to be safe for potential use in IV formulations. Likewise, toxicity studies in animals have shown that M1944 CS (Gattefosse, FR) is well tolerated and could have potential for inclusion in parenteral formulations. The other excipients are currently used in approved parenteral formulations.

TABLE 2

Composition of Candidate Undiluted Premix Parenteral DIM Formulations
Ingredients Specified as Percentages of Contained in the Formulation

| Excipient Ingredient | Formulation # | | | | | | | | | |
|---|---|---|---|---|---|---|---|---|---|---|
| | 1 | 2 | 3 | 4 | 5 | 6 | 7 | 8 | 9 | 10 |
| Ethanol | 65 | 62 | 42 | 39 | 49 | 59 | 40 | 45 | 30 | 49 |
| Gattefosse Transcutol | | | 10 | | | | 13 | | 15 | 17 |
| Gattefosse WL 1349 | 6 | 4 | 4 | | | 9 | 16 | 10 | 10 | 12 |
| Gattefosse M1944CS | | | | 10 | 9 | | | | | |
| Phosphatidyl Choline | 7 | 7 | 7 | 7 | 8 | 8 | 8 | 8 | 8 | |
| BASF HS-15 | | 5 | 5 | 12 | 10 | | 21 | 15 | 15 | 17 |
| Poloxamer 188 (Vepoloxamer P-188) | 6 | 6 | 12 | 8 | 10 | 11 | | 8 | 8 | 8 |
| Poloxamer 407 | 14 | 14 | 28 | 12 | 12 | 11 | | 12 | 12 | 12 |
| Diindolylmethane | 2 | 2 | 2 | 2 | 2 | 2 | 2 | 2 | 2 | 2 |

Method of Manufacture and Preliminary Evaluation of Undiluted DIM Premix Formulations The ten candidate formulations were prepared by adding each of the ingredients to the ethanol with stirring. After the final ingredient, the mixture was stirred to uniformity for 10 minutes using a magnetic spin bar. The product mixture was examined for clarity and fluidity after 2 hours at room temperature. Observations included the following: Formulation #1, #2, #6, #7, #8—all produced clear solutions, Formulation #4 contained some suspended solids, Formulations #5 and #10 were opaque. Formulations #3 and #9 were semi-solid. From these observations it was concluded that some amount of medium chain triglyceride and/or phosphatidyl choline is needed to accomplish complete dissolution of API DIM; larger amounts of ethanol are needed relative to the poloxamers to prevent gelation of the premix, and Transcutol does not function to prevent gelation. Based on the observations Formulations #3, #5, #9, and #10 were considered poor candidates for further development.

Dispersion Testing of Candidate Premix Formulations

Each of the formulations were dispersed in 0.9% saline by pipetting 1 mL of the candidate solution into 8 mL of saline. The pipette was rinsed with 1 mL of saline and the suspension was shaken vigorously by hand for 5 minutes. The semi-solid formulations were warmed slightly in a water bath to become fluid prior to dispersion in saline solution. The uniform suspensions produced all contained 20 mg DIM per mL. Each suspension was examined by light microscopy for any visible particulates. The microscope slides were immediately examined after preparation and then again at 2 hour and 4 hour time intervals following dispersion and without further mixing. Additionally, a prototype premix using the #8 formulation was prepared but this time including DIM with additional all trans retinoic acid (ATRA) added at half the concentration of the DIM. The dissolution of both DIM and ATRA indicated reserve excipient capacity to accommodate a lipophilic second active API in the #8 formulation. This combined formulation was tested similarly to the other samples for dispersion. Other appropriate second active APIs for addition to Formulation #8 and co-administration with DIM include 1,1-bis(3,3'-indolyl)ethane ("HB-237"), EP-7041 (eXlthera Pharamaceuticals), and LPN023 (Novartis).

Observations following dispersion in saline of candidate DIM Premix formulations from Formulations in Table 2 are summarized in the following Table 3:

TABLE 3

Summary of Dispersion Testing Observations

| Unfavorable Observation | Formulation # | Crystals Observed | Particles Observed | Oil drops or Oily Texture Observed | HS 15 Used in Prototype with % H-15 |
|---|---|---|---|---|---|
| + | 1 | 0 | + 2-5 μm | + | 0 |
| +* | 2 | 0 | 0 | + | + (5%) |
| +* | 3 | 0 | + | 0 | + (5%) |
| +* | 4 | 0 | + | + | + (12%) |
| +* | 5 | 0 | + | 0 | + (10%) |
| + | 6 | + | + | + | 0 |
| +* | 7 | + | + | + | + (21%) |

TABLE 3-continued

Summary of Dispersion Testing Observations

| Unfavorable Observation | Formulation # | Crystals Observed | Particles Observed | Oil drops or Oily Texture Observed | HS 15 Used in Prototype with % H-15 |
|---|---|---|---|---|---|
|  | 8 | 0 | 0 | 0 | + (15%) |
| +* | 9 | 0 | + | 0 | + (15%) |
| +* | 10 | 0 | 0 | + 2-5 µm | + (17%) |
| +* | 11 | ++ | + | 0 | 0 |

\* = Unfavorable Observation associated with use of Kolliphor H-15
+ = "Yes, observed"
0 = none or negative Of the ten Formulations tested, Formulation 8 provided the most stable pre-mix formulation suitable as a premix for an IV formulation of DIM. Other prototypes tested with either more or less Kolliphor® HS 15 failed to show all the preferred attributes of Formulation 8 with observation of one or more of crystals, particles, and/or oil drops observed in the Formulation after 1-4 hours following dispersion at room temperature. When crystals formed, they were needle shaped—with dimensions in the range of 1 to 2 microns by 3 to 10 microns in length.

The results in Table 3 show the unexpected superiority of Formulation 8. Formulation 8 provided a stable pre-mix formulation suitable for more formal dispersion testing.

Based on these observations, Formulation #8 was chosen for further evaluation. A solution of heparinized saline was prepared at 10 units of heparin per mL of saline. The 1 mL sample of Formulation #8 was dispersed similarly in the heparinized saline as before in regular saline. There were no discernible differences in the initial dispersion or its stability with no DIM crystal precipitate discernible when subjected to light microscopic examination Evaluation of a Dispersed IV DIM Formulation Using Dynamic Light Scattering Particle Size Analysis Dynamic Light Scattering (DLS) is also known as Photon Correlation Spectroscopy. DLS is used to characterize the size of various particles including proteins, polymers, micelles, carbohydrates, and nanoparticles. Solutions of poloxamers generally form micelles and depending on a number of factors such as concentration, temperature and composition. Micelles have particle sizes in the range of 200 nanometers (Almeida, M., Magalhães, M., Veiga, F. et al. Poloxamers, poloxamines and polymeric micelles: Definition, structure and therapeutic applications in cancer. J. Polym. Res. 25, 31 (2018)). Particle size of Poloxamer 407 suspensions have been reported in dilute solution and show a size of approximately 300 nm (Dukhin, A. S., Goetz, P. J. Applications for Emulsions and Other Soft Particles, in Characterization of Liquids, Dispersions, Emulsions, and Porous Materials Using Ultrasound (Third Edition), 2017). In addition to particle size by DLS, the Polydispersity Index (PDI) is a parameter used to define the size range of lipidic nanocarrier systems. The term "polydispersity" or "dispersity" is used to describe the degree of non-uniformity of the size distribution of particles. In safety and regulatory review of drug delivery applications using lipid-based carriers, a PDI of 0.3 and below is considered to be acceptable and indicates a homogenous population of particles.

Figure 3:
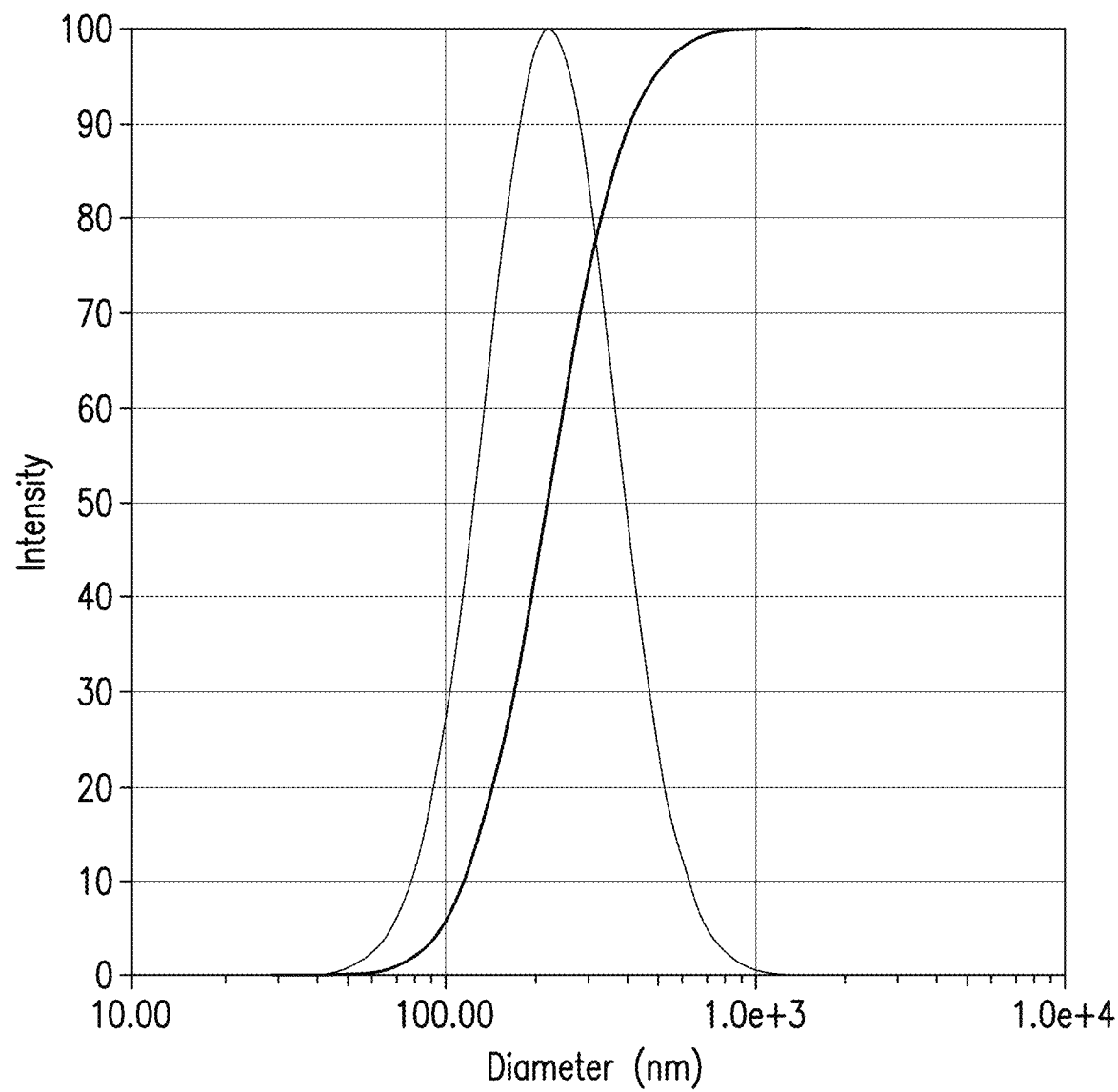
FIG. 3 shows the Dynamic Light Scattering (DLS) Report Graph from the particle size and polydispersity testing following dispersion of 1ml of the Formula #8 premix into 100 ml of physiologic saline. Using a Brookhaven Instrument DLS apparatus, the measurement showed an Effective (Eff) diameter of 218.25 nm and a Polydispersity Index (PDI) of 0.259.

Formulation #8 (see Table 2) was carried forward into Particle Size and PDI evaluation. Formulation #8 was diluted 1 mL into 100 mL of standard saline and gently mixed with a magnetic spin bar. The particle size was measured using a Brookhaven Dynamic Light Scattering instrument. The results showed an Effective (Eff.) Diameter of 218.25 nm. The PDI was determined at 0.259 nm which is under the FDA upper limit guidance of 0.3 for this type of product (see, e.g., FIG. 3).

Conclusions Regarding DIM Premix Formulation and Dispersion Testing

The #8 formulation produced the cleanest dispersion observed using microscopy with no crystals of DIM forming at up to 4 hours. These observations were confirmed by subsequent dynamic light scattering measurement of particle size in a standard suspension of 100 mL, emulating clinical use. It is concluded that the use of the Kolliphor HS-15 and the phosphatidyl choline produce smaller particle size micellar suspensions and the use of the poloxamers improves the clarity of the dispersion and may prevent drug precipitation. There is a minimum amount of ethanol required at 45 to 50% for the candidate drug product to remain fluid and uniform in the premix. In conclusion, Formulation #8 proved to be one of the best of the premix formulations and utilizes previously approved excipients with a history of safe use in parenteral drug products. Formulation #8 consists of a mixture of ethanol, Kolliphor HS-15, Gattefosee WL 1349, phosphatidyl choline, Kolliphor P188, Kolliphor P407, and Diindolylmethane (DIM).

Projected Clinical Use of a DIM Premix Drug Product

The DIM premix formulation is intended for early initiation of DIM-based NHCHI therapy in critically ill patients not able to safely take oral medication. The goal of administration is to optimize DIM blood and tissue levels as quickly as possible following imaging studies showing absence of intracranial hemorrhage. In addition, injured patients being kept NPO for surgery for non-CNS injuries and patients needing transport to second hospitals can receive TBI therapy from intravenous DIM during transport.

Indications and Methods of Use for Parenteral DIM Formulations

DIM Parenteral Premix (2% DIM) is an intravenous drug product for the treatment of CHI.

The dosage form consists of a concentrated sterile premix provided in amber glass single use vials containing 2% Diindolylmethane (DIM) dissolved in sterile excipients. Typical use includes sterile transfer of vial contents into room temperature or warmed 50-100 cc bags of sterile 0.9% normal saline for injection.

Typical starting dose in human subjects involves administration of 25-200 mg DIM in 50-100 cc of saline suspension over 15-60 minutes. Starting dose optionally is followed by a controlled rate maintenance infusion.

Example 6

Clinically Relevant Translational Animal Model Demonstrating Efficacy of DIM in NHCHI Introduction: An established experimental murine model is utilized to demonstrate the efficacy and safety of oral DIM and DIM/aripiprazole drug products in NHCHI. Conduct of the controlled cortical impact (CCI) injury in anesthetized animals emulates the mechanisms of CHI in humans and produces both the Acute Phase Response (APR) and more prolonged secondary phase injury. Release of neuro-inflammatory Extracellular Vesicles (EVs), early onset of cerebral edema, and blood brain barrier (BBB) breakdown emulate the clinical condition in this model. In addition, components of the prolonged secondary injury phase that is characterized by long-term cognitive deficits and/or depression are induced and objectively assessed with established neurobehavioral evaluation methods. The methods employed are clinically relevant because CHI patients often present with a loss of concentration, retrograde amnesia, and reduced short-term memory after injury. Development of cognitive deficits after TBI is paralleled in rodent models as reflected in cognitive tasks including the novel objection recognition (NOR) test, Open Field Test, and development of depression as reflected in the Tail Suspension test. (Fenn A M, Skendelas J P, Moussa D N, Muccigrosso M M, Popovich P G, Lifshitz J, Eiferman D S, Godbout J P. Methylene blue attenuates traumatic brain injury-associated neuroinflammation and acute depressive-like behavior in mice. J. Neurotrauma. 2015 Jan. 15; 32(2):127-38.) In order to evaluate the hyper-acute contribution of post-injury release of EVs, established methods to demonstrate the presence and quantities of CHI related EVs are utilized (Coumans F A W, Brisson A R, Buzas E I, Dignat-George F, Drees E E E, El-Andaloussi S, Emanueli C, Gasecka A, Hendrix A, Hill A F, Lacroix R, Lee Y, van Leeuwen T G, Mackman N, Mager I, Nolan J P, van der Pol E, Pegtel D M, Sahoo S, Siljander P R M, Sturk G, de Wever O, Nieuwland R. Methodological Guidelines to Study Extracellular Vesicles. Circ. Res. 2017 May 12; 120(10):1632-1648). A more robust treatment response is possible with the use of DIM combined with aripiprazole in a SMEDDS formulation, and therefore the model to be employed will include experimental groups receiving aripiprazole alone and DIM plus aripiprazole. As contemplated, use of aripiprazole contributes partial agonist activity at D2 and 5-hydroxytryptamine$_{1A}$ (5-HT$_{1A}$) receptors shown to be effective in the treatment of cognitive deficits in a model of CHI (Phelps T I, Bondi C O, Mattiola V V, Kline A E. Relative to Typical Antipsychotic Drugs, Aripiprazole Is a Safer Alternative for Alleviating Behavioral Disturbances After Experimental Brain Trauma. Neurorehabil. Neural Repair. 2017 January; 31(1):25-33.). The following illustrates the experimental plan to be followed.

Animals: Studies will be performed using adult male mice ~3 months old. Mice are individually housed in polypropylene cages for the study and maintained at 25° C. under a 12 h light/12 h dark cycle with ad libitum access to water and rodent chow. All procedures are in accordance with the National Institute of Health Guidelines for the Care and Use of Laboratory Animals.

Method of CCI to be used: A CCI injury is induced with mice receiving a midline diffuse TBI using an established apparatus. This diffuse CCI injury to be induced is severe enough to cause contusion but does not cause subarachnoid or intracerebral hemorrhage. It is sufficient to cause diffuse axonal injury in the neocortex, hippocampus, and dorsolateral thalamus. A midline craniectomy is performed and the CCI is conducted. All sham controls received the same procedure without the CCI step. After emerging from anesthesia and before proceeding to initial oral dosing mice are evaluated for injury severity using a self-righting test. Mice meeting self-righting inclusion criteria proceed to initial dosing ~60 minutes after emerging from anesthesia and are entered into the following experimental groups.

Experimental Groups:
1. Sham Control—craniotomy with no induced injury—water per os (po) by gavage
2. Vehicle Control—craniotomy with induced CCI—doses with vehicle in water po
3. Low Dose SMEDDS DIM (Example 1)—craniotomy with induced CCI—dosed at 30 min PI (Post Injury), 12 hr PI, q am PI for 7 days in water po
4. High Dose SMEDDS DIM (Example 1)—craniotomy with induced CCI dosed at 30 min PI, 12 hr PI, q am PI for 7 days in water po
5. Low Dose SMEDDS aripiprazole (Example 2, Formula A)—craniotomy with induced CHI dosed at 30 min PI, 12 hr PI, q am PI for 7 days in water po
6. SMEDDS DIM plus aripiprazole (Example 2, Formula B)—craniotomy with induced CCI dosed at 30 min PI, 12 hr PI, q am PI for 7 days in water po 24 hour post CCI evaluation: At ~24 hours after first dose a subset of each group is euthanized, blood is obtained by cardiac puncture, the circulation is perfused with heparinized saline, and brain specimens are obtained and fixed for sectioning, staining, and histologic examination.

Quantification of blood-brain barrier (BBB) breakdown at 24 hrs: IgG staining density is used as a marker for BBB breakdown and following brain sectioning and background staining with cresyl violet, immune histochemical staining for presence of IgG is conducted along with additional immunohistochemical staining. The brain tissue staining is analyzed using imageJ (version 1.8.0_101; NIH, Bethesda, MD) software on images of whole coronal sections. Total area of IgG stain was measured, as well as stain intensity to quantify the amount of tissue IgG which relates to leakage across the BBB.

Cerebral Edema Estimation at 24 hrs: Edema is classified as increased water content in the brain and is determined as follows. 24 hrs after sham or CCI, a portion of euthanized mice brain specimens not sectioned for IgG and Immunohistochemical staining, using the rostral and caudal cortex is dissected. Tissue is weighed and oven dried overnight at 73° C. before reweighing. The loss of weight on drying as a percent of fresh weight is determined and used as a measure of cerebral edema induced by CCI.

Extracellular vesicle isolation and quantification at 24 hrs: Blood from animals euthanized at 24 hours is centrifuged at 2700 g for 10 min at 4° C. to separate plasma and remove platelets. Platelet-free plasma is then ultracentrifuged at 120,000 g for 120 min to pellet the EVs, which are then resuspended in phosphate-buffered saline (PBS). Using established methods for quantitation of EVs the concentration of EVs in ultracentrifuged plasma samples is determined utilizing established methods including labeling and FACs cell sizing and sorting and/or Tuneable resistive pulse sensing or other accepted methods. Details of accepted methods are presented and well known in the field (Coumans F A W, et al supra).

Neurobehavioral Assessment at 7 days Post Injury: Following the last dose of study material, mice are evaluated for neurobehavioral function. Motor function, coordination and balance utilizing the Rotarod test. Cognitive assays include one or more of the Novel objection recognition (NOR) and/or the Open-field test as typically performed.

Rotorod—Mice are trained on the apparatus each day for 3 d before testing. Mice are placed on an accelerating rotarod cylinder that is slowly increased from 4 to 40 rpm over a 5-min trial. The length of time balance was maintained while walking on top of the drum was recorded. A trial stops once the mouse falls off or grips the cylinder for two consecutive revolutions. Optionally, motor coordination is determined by measuring the time required to traverse a stationary 1-m narrow beam (6-mm width). Each mouse is tested three times. The average time to traverse the beam and number of paw slips are recorded. Hanging wire test: Grip strength is assessed by placing mice on an apparatus consisting of a 50-cm string pulled between two vertical supports.

NOR—To test cognition, novel objection recognition (NOR) is performed. Cognitive function is determined using a two-object novel object recognition (NOR) task, which assesses recognition memory. Mice were placed in an enclosed box with two identical objects that were placed within a 10 cm circle, located a set distance apart. Mice are then removed from the environment for a set amount of time, and one of the two previously used (familiar) objects is replaced with a novel object that was different from the familiar object in shape, texture, and appearance. The ability of the mouse to discriminate between the familiar and novel object is quantified as a discrimination index, $DI=(Tn-Tf)/(Tn+Tf)$, where Tn is the time spent by the mouse with the novel object, and Tf indicates the time spent with the familiar object. All behavioral analyses are done by blinded investigators.

Open Field Test—Optional further cognitive outcome testing uses the Open Field Test. Open-field test Mice are tested in a square box (40 cm by 40 cm by 40 cm) for 10 min, and activity is digitally recorded. Distance traveled, mean velocity, and time spent in the center zone are determined, group data assembled and compared.

Assessment for Depression is evaluated using the tail suspension test. Depressive-like behavior is measured using the tail suspension test (TST). 7 d after sham or TBI, mice are suspended by their tail and video recorded for 10 min. The number of mice remaining immobile and amount of time spent immobile is assessed by a trained observer blind to experimental conditions. Increased time spent immobile designates an increase in depressive-like behavior.

Statistical analysis All data are analyzed using GraphPad Prism 8 software. Multigroup comparisons are made using a one-way analysis of variance (ANOVA), with adjustments for multiple comparisons. Data are further analyzed by Tukey's post hoc test. Two group comparisons are analyzed by Student's t test. Associations between serum DNase, ICP, and GCS score are evaluated using Pearson correlation coefficients. Results are expressed as mean±SEM. A $P<0.05$ was considered to be statistically significant.

Discussion: The measures of hyper-acute, brain specific changes in level of edema, synonymous with brain swelling (cerebral edema), and loss of integrity of the BBB are anticipated to be reduced by DIM's biological activity during therapy. These treatment responses are highly relevant to clinical outcomes in NHCHI since increases in intra-cranial pressure which lead to brain swelling are associated with poor neurological outcome. The reduction in early increases in circulating EV's anticipated is precedent setting and represents a novel means of interrupting the innate immune-inflammatory cascade initiated by CHI. Improvement in neurobehavioral outcomes with DIM intervention in CHI represent the central goal of DIM therapy and fills a critical unmet need in the current acute care of CHI and TBI.

Example 7

Translational Study of 3,3'-Diindolylmethane for the Treatment of Moderate-to-Severe TBI in the Sprague Dawley Rat Introduction Evaluation of 3,3'-diindolylmethane (DIM) in a clinically relevant animal model of Traumatic Brain Injury (TBI) utilized the Lateral Fluid Percussion (LFP) brain injury method. LFP is the most established and frequently used method for evaluating mixed focal and diffuse brain injury (Thompson H J, Lifshitz J, Marklund N, Grady M S, Graham D I, Hovda D A, McIntosh T K. Lateral fluid percussion brain injury: a 15-year review and evaluation. J Neurotrauma. 2005 January; 22(1):42-75.). Using rats, the parasagittal LFP model recreates the physiological, pathological, and neurobehavioral sequela of TBI in humans. LFP is an accepted method for producing evidence of therapeutic response which translates to clinical response in subsequent clinical trials. DIM was studied using the parenteral anhydrous DIM Premix formulation "DIM Premix" (see Example 4) for its effects on acute TBI injury and recovery. This study implemented IV and IP administration of diluted DIM Premix (30 mg/kg and 60 mg/kg DIM, respectively). Over the days following surgery, rats were assessed for sensorimotor deficits, associative learning and memory, cortical and hippocampal edema, Extracellular Vesicle (EV) levels, and histopathological damage.

Test Animals

Adult male Sprague Dawley rats (270-350 gms) were purchased from Charles Rivers Laboratories and allowed to habituate for 3-9 days upon arrival in the animal facility. Rats were provided with free access to food and water and placed on 12/12-h light/dark cycle within a humidity- and temperature-controlled environment. This study was conducted in accordance with Assessment and Accreditation of Laboratory Animal Care, Institutional Animal Care and Use Committee (IACUC) guidelines.

Study Design

Model Induction/Surgery

Adult, male Sprague Dawley rats (270-350 g) were anesthetized with 3% isoflurane and 70% nitrous oxide, the hair on the head was shaved, and the rat was placed into a stereotaxic frame under 1-3% isoflurane. Body temperature was maintained at 37° C. The skin was cleaned with chlorohexidine and then a 1.5-2.5 cm midline incision was made through the skin and muscle of the scalp. The skin and muscle were retracted to expose the skull and provide a clear surgical field. A 4.8 mm craniectomy was created using a trephine over the right hemisphere at −3.8 mm posterior to bregma and 2.5 mm lateral to the midline. A sterile plastic injury tube (the plastic connector of a sterile needle cut 1 cm in length and trimmed to fill the craniotomy perfectly) was placed over the exposed dura and bonded by cyanoacrylate adhesive to the skull. Dental acrylic was poured around the injury tube to obtain a perfect seal. After the acrylic hardened, the scalp was sutured back using staples. The animals were then returned to their home cage.

Approximately 12-24 h after the preparation surgery, the rats were anesthetized with 3% isoflurane, 70% nitrous oxide and 30% oxygen, intubated, connected to a respirator, and ventilated to be maintained on 1-3% isoflurane in a mixture of 70% nitrous oxide and oxygen. The tail artery was cannulated to monitor arterial blood pressure and blood gases and to administer diluted DIM Premix. For preparation of the incision to place the cannulas, the skin at the incision site was shaved and swabbed with chlorohexidine solution. The animal was paralyzed for mechanical ventilation with pancuronium (1 mg/kg, intravenously) to maintain arterial blood gases and blood pH within normal limits. Following administration of pancuronium, TBI DIM Premix and Vehicle group rats inspired oxygen was reduced to 21% to maintain blood $pO_2$ levels at approximately 85-95 mmHg. $pCO_2$ levels were monitored to remain at physiological levels of 34 to 46 mmHg. Sham animals received 3% isoflurane, 70% nitrous oxide and 30% oxygen without reduction of oxygen to 21%. Brain temperature was indirectly measured by a thermistor placed in the left temporalis muscle, and rectal temperature will be measured by a thermistor place in the rectum. Feedback-regulated heating lamps placed over the head and body were used to control temperature. Body and head temperature were held at normothermia (37° C.) for the duration of the surgery. Following a normalization period (15-30 min), the rats were then connected to the fluid-percussion injury device. A small volume of saline impacted the dura in the cranial cavity and produced a brief displacement (16 msec, 2.2-2.4 atm) of neural tissue. The amplitude of the resulting pressure pulse was measured in atmospheres by a pressure transducer and recorded on a PowerLab chart recording system. Sham animals underwent all surgical procedures but were not subjected to the fluid percussion pulse. After either the TBI or sham injury, the injury cap was removed, and the scalp was closed using staples. For tail artery incisions, the tail was sutured together with nylon sutures. To prevent any possible infections in the Sprague Dawley rats, penicillin/benzathine (20,000 IU/kg, intramuscular, IM) was administered immediately after the surgery. Rats were maintained on ventilation for at least 15 min after the injury. DIM from DIM Premix (Active) at 30 mg/kg diluted 1:2 with sterile saline and Premix-Vehicle Only (Control) at equivalent volume were administered at ~10 min post-TBI by slow IV push. Rats were returned to an individual home cage until fully recovered, supplied with food and water, and given buprenorphine (0.01 mg/kg, subcutaneously) when recovered. At 4 h post-injury the TBI DIM Premix rats were administered diluted DIM Premix at with DIM at 60 mg/kg IP. At 4 h post-injury, TBI Vehicle rats were administered diluted Premix-Vehicle Only at a volume equivalent to the 30 mg/kg DIM dose from DIM Premix (BR4044). Rats were observed for 24 h post-operatively, and then returned to the vivarium.

Group Size Rationale

A sample size of 12 evaluable rats in each treatment group for the behavioral outcome measures was estimated to have 90% power to detect a true treatment difference of at least 39 seconds (at the 1-sided, 0.05 significance level) between the TBI Vehicle Only group and TBI DIM Premix-treated group for percent freezing in the context when tested 24 h after training. This estimate used Dunnett's correction for comparing the treatment group to a control group and assumed a standard deviation (SD) of 15 seconds. A sample size of 5 evaluable rats in the treatment group for the edema measurements and EV analyses was estimated based on recent prior studies for the edema measurements. The study therefore required 17 rats in each group to be randomized and evaluable for the study. To achieve this using a surgery model with a 30% attrition rate, 22 rats were expected to be used for each group for a total of 66 rats.

Experimental Procedures

TABLE 4

Schedule of events for rats used in the Brain Edema and EV studies

| | Events | | | |
|---|---|---|---|---|
| Timing | 10 min post-surgery | 4 h post-surgery | 1 d post-surgery, AM | 1 d post-surgery, PM |
| Event | IV injection | IP injection | IP injection | Sacrifice (edema, blood for EVs) |
| | Groups | | | |
| DIM Premix | 30 mg/kg DIM IV | 60 mg/kg DIM IP | 60 mg/kg DIM IP | |
| Vehicle Only | Equivalent Volume to a 30 mg/kg IV dose Over 5 min | Equivalent Volume to a 30 mg/kg IP dose IP | Equivalent Volume to a 30 mg/kg IP dose IP | |
| Sham | Normal Saline 1.5 cc Over 5 min | Normal Saline 1.5 cc IP | Normal Saline 1.5 cc IP | |

TABLE 5

Schedule of events for rats used in behavior and histology analyses

| | Events | | | | | | | |
|---|---|---|---|---|---|---|---|---|
| Timing | 3-7 d pre-surgery | 10 min post-surgery | 4 h post-surgery | 2 d post-surgery BID | 3 d post-surgery BID | 4 d post-surgery | 7-9 d post-surgery | 10 d post-surgery |
| Event | Cylinder task baseline | IV injection | IP injection | IP injection | IP injection | Cylinder task | Cue and contextual fear conditioning | Sacrifice (histology, contusion volume) |

TABLE 5-continued

Schedule of events for rats used in behavior and histology analyses

| | | | Groups | | |
|---|---|---|---|---|---|
| DIM Premix | TBI | 30 mg/kg | 60 mg/kg | 60 mg/kg | 60 mg/kg |
| Vehicle Only | TBI | Equivalent Volume to a 30 mg/kg IV dose Over 5 min | Equivalent Volume to a 30 mg/kg IP dose | Equivalent Volume to a 30 mg/kg IP dose | Equivalent Volume to a 30 mg/kg IP dose |
| Sham | | Normal saline 1.5 cc IV dose Over 5 min | Normal saline 1.5 cc IP | Normal saline 1.5 cc IP | Normal saline 1.5 cc IP |

Brain Edema Measurements

At ~24 h after surgery with injury or sham surgery (with afternoon sacrifice first day after injury to be at least 24 h following first dose and following a second IP dose), rats were re-anesthetized with 3% isoflurane, 70% nitrous oxide for 5 min, decapitated, and the brain was removed and placed in a glass petri dish. The right parietal cortex and hippocampus were dissected and placed onto pre-weighed aluminum foil squares for immediate weighing using an analytical balance. The samples and foil were placed in a 100° C. vacuum oven for 72 h until completely dry, and then re-weighed to calculate the percent wet weight. The contralateral parietal cortex and hippocampus were dissected and fixed in formaldehyde for future analysis.

Extracellular Vesicle (EV) Isolation and Measurement

The isolation and analysis of Extracellular Vesicles (EVs) was undertaken to demonstrate correlation of rising levels and size change of EVs to acute damage associated with Fluid Percussion Injury (FPI) (Zhao Z et al, supra). The present study animals which were sacrificed in the afternoon at 1 day post-surgery provided blood for isolation of EVs. At the time of sacrifice, trunk blood was collected in plasma EDTA tubes (Sarstedt) and centrifuged. Plasma was stored at −80oC until processing for isolation of EVs using the Total Exosome isolation kit (from Plasma) (Invitrogen). Assessment of EV size and particle concentration was carried out by Nanoparticle Tracking Analysis (NTA) using NanoSight technology (Malvern Panalytical). Excess plasma was stored frozen for possible future additional analysis.

Cylinder Task

The Cylinder Task assesses preservation of sensorimotor function and plasticity acutely and chronically in unilateral rat models of central nervous system injury. (Schallert T, Fleming S M, Leasure J L, Tillerson J L, Bland S T. CNS plasticity and assessment of forelimb sensorimotor outcome in unilateral rat models of stroke, cortical ablation, and parkinsonism. Neuropharmacology. 2000 Mar. 3; 39(5):777-87). Animals were evaluated for spontaneous forelimb placement in a transparent Plexiglas cylinder (20 cm diameter×30 cm height) for 5 min. Animals were first evaluated for baseline behavior in the cylinder test at 3-7 days prior to surgery, and then re-evaluated at day 4 post-surgery at least 8 h after last IP dose to avoid any sedative effect from last drug dose. The number of times the right or left forelimb contacted the wall was counted. Asymmetry index was calculated by dividing the number of contralateral (left) forelimb touches by total forelimb touches. For each animal, asymmetry index post-surgery was normalized to baseline asymmetry index to account for any pre-operative bias.

Cue and Contextual Fear Conditioning

Patients with PTSD display both enhanced fear responses and impaired extinction of fearful memories. These components of memory can be recapitulated in rodents using fear conditioning paradigms to emulate anxiety disorders including PTSD (Meyer D L, Davies D R, Barr J L, Manzerra P, Forster G L. Mild traumatic brain injury in the rat alters neuronal number in the limbic system and increases conditioned fear and anxiety-like behaviors. Exp Neurol. 2012 June; 235(2):574-87.) On Day 7, animals were habituated for 10 min to a cage equipped with a shock grid floor (Harvard Apparatus). At 24 hrs after habituation on Day 8, animals were trained by being placed in the apparatus for 120 s, and then a 30 s tone (75 dB, 2.8 kHz) was delivered that co-terminated with a 1 mA, 1 second (s) foot shock. Animals remained in the apparatus for 60 s after the foot shock. At 24 h after training on Day 9, animals were placed in the apparatus and freezing was measured for 210 s to assess contextual fear conditioning. At 1 h after contextual fear memory testing, animals were placed in an altered apparatus, and freezing was measured prior to (90 s) and during replay of the tone (120 s). Freezing behavior was quantified by video analysis (FreezeFrame, Actimetrics).

Histology Analysis

On Day 10, animals were deeply anesthetized, and brains were dissected and fixed in 4% formalin. Brains were embedded in paraffin and sectioned in a stereological series (5 series, 10 μm thick sections, 150 μm apart). One series of sections was stained with hematoxylin and eosin. Slides were analyzed at 4×magnification using NeuroLucida to quantify cortical contusion volume and/or cortical atrophy as determined by the pathology. Another series of sections was immunostained with NeuN. Sections spanning bregma levels −3.3 to −6.8 mm for rats were analyzed, centered around the brain injury region. Hippocampal regions (dentate hilus and CA3) and the parietal cortex were quantified for neuronal loss using NeuN immunostaining and non-biased stereology with StereoInvestigator at 63×magnification.

Safety Considerations

A priori defined behavioral criteria for early removal from the experiments were employed and included: mortality, autotomy, excessive grooming leading to loss of dermal layers, spontaneous vocalization when touched, loss of >15% of body weight, inability to feed or drink, poor grooming habits, listlessness, excessive activity, motor paralysis, a non-resolving infection at the surgical site, rapid than normal respiratory rate and/or porphyrin accumulation, behavioral deficits in sham rats, and no behavioral deficits in TBI-vehicle treated rats. These criteria were applied before or after surgery and drug dosing. A priori defined pathology criteria for removal from the study were: cortical pathology in sham rats, no cortical pathology in TBI-vehicle rats.

Statistical Analysis

Statistical comparisons were made using GraphPad Prism 10.0.2. Edema, asymmetry index, EV concentration/size/number were analyzed with a one-way ANOVA (Analysis of variance) and post-hoc Bonferroni's correction for multiple comparisons. Fear conditioning was analyzed with a two-way repeated measures ANOVA with the factors animal treatment x trial and post-hoc Bonferroni's correction for multiple comparisons when significant interactions were present. Pathology scores of animals that received TBI were analyzed with a Mann-Whitney test. A 2-sided p-value of<0.05, adjusted by Bonferroni's multiple comparison test was considered significant. Normality was tested by the Shapiro-Wilk normality test. Data that was not normally distributed was then normalized using a logarithmic transformation.

Results

Model-Related Mortality Rates

The study began with a total of 61 rats. Of these, 4 died from TBI surgery. These deaths occurred after randomization to the TBI and drug or vehicle treatment group, but before drug or vehicle dosing. This accounts for 6.6% mortality of all rats and 9.8% mortality of the TBI rats.

Brain Edema

Figure 4:
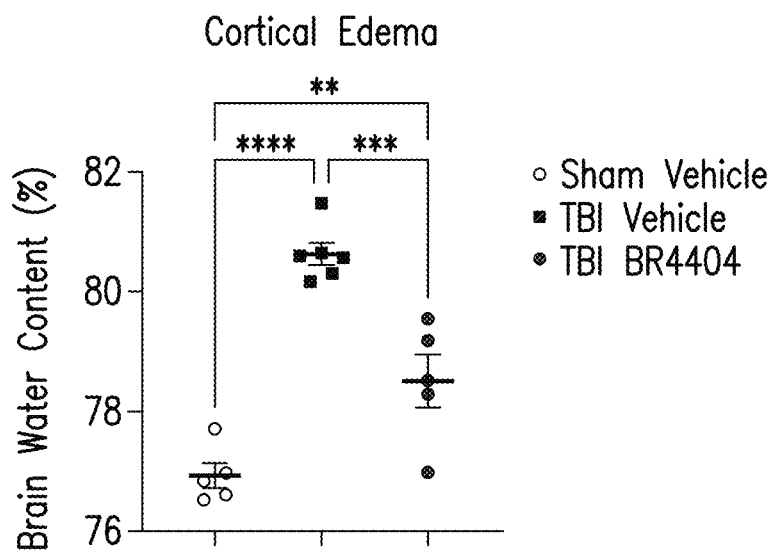
FIG. 4 shows cortical brain water content (%) quantifying Cortical Edema in the ipsilateral cortex for sham vehicle, TBI vehicle and TBI BR4404 treated rats. Adjusted p values: **<0.0001, *<0.001, **<0.01.

Results showed a significant decrease in the % brain water content corresponding to less edema in the ipsilateral cortex for the TBI DIM Premix group (BR4044) versus the TBI Vehicle group (p<0.0001). See FIG. 4.

Figure 5:
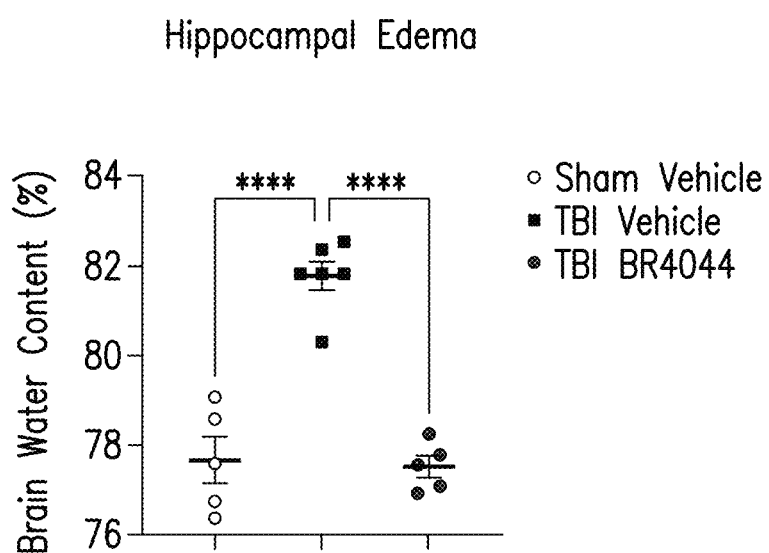
FIG. 5 shows hippocampal zone brain water content (%) quantifying Hippocampal Edema in the ipsilateral hippocampus for sham vehicle, TBI vehicle and TBI BR4404 treated rats. Adjusted p value: ****<0.0001.

Results showed a significant decrease in the % brain water content in the ipsilateral hippocampus for the TBI DIM Premix group (BR4044) versus the TBI Vehicle group (p<0.0001). DIM treatment resulted in the TBI DIM Premix group and the uninjured Sham Vehicle group having essentially the same % brain water content in hippocampal tissue with a non-significant difference (p>0.9999). See FIG. 5.

Cylinder Task Analysis

Figure 6:
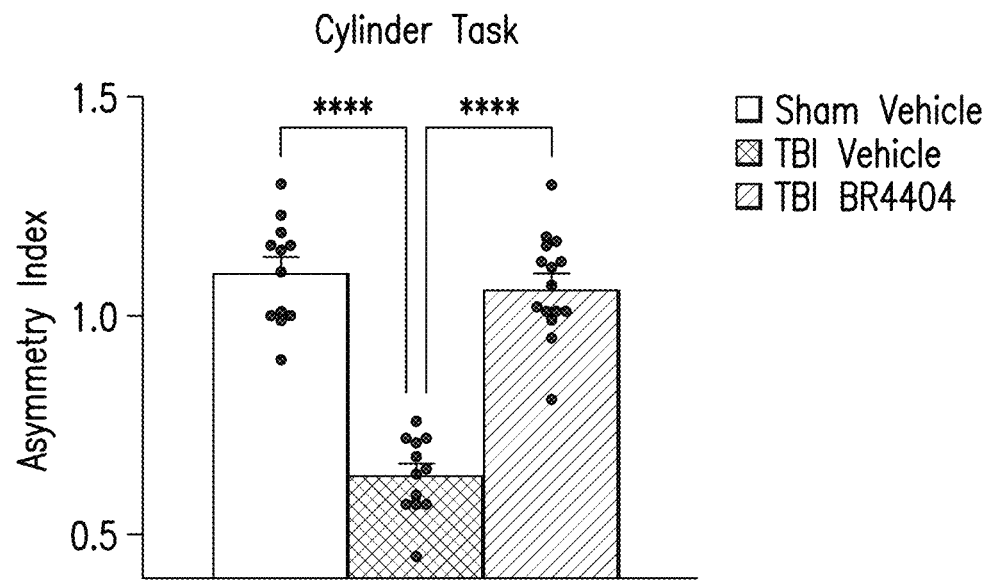
FIG. 6 shows the Cylinder Task determined asymmetry index for sham vehicle, TBI vehicle and TBI BR4404 treated rats. Adjusted p value: ****<0.0001.

There was a significant improvement in the cylinder task asymmetry index in the TBI DIM Premix group (BR4044) as compared to the TBI Vehicle group (p<0.0001). There was a nonsignificant different in the asymmetry index between the TBI DIM Premix group and the Sham Vehicle group (p>0.9999). See FIG. 6.

Contextual Fear Conditioning Analysis

Figure 7:
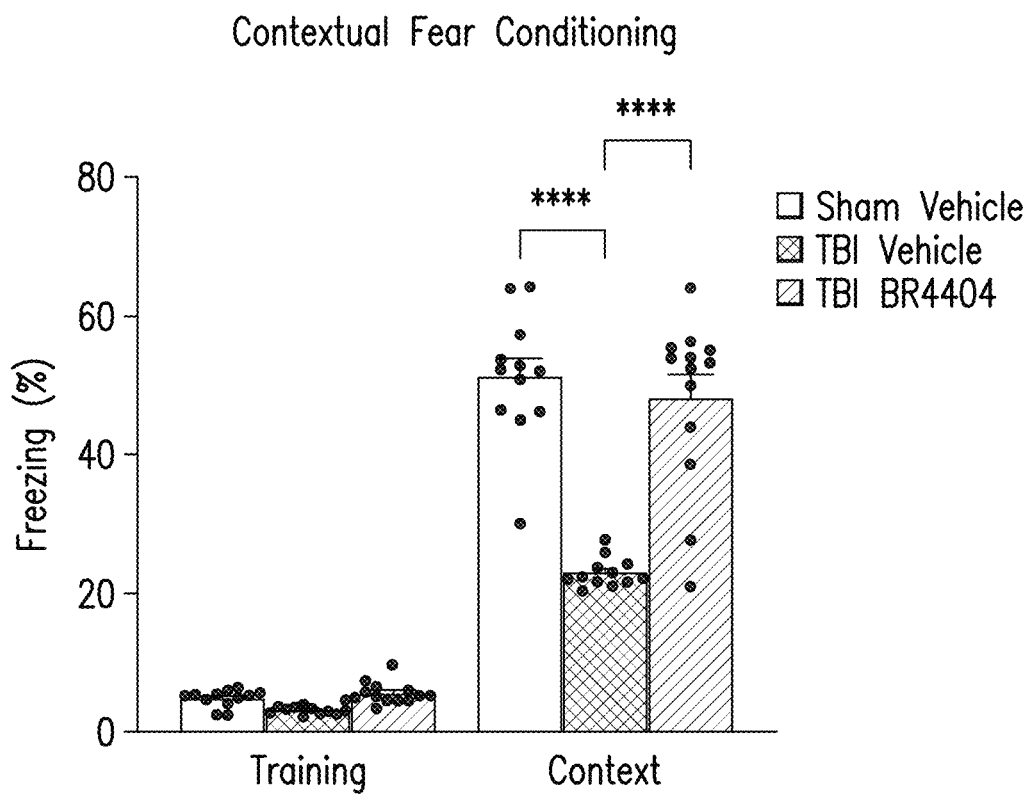
FIG. 7 shows Contextual Fear Conditioning learning and memory measured as % freezing for sham vehicle, TBI vehicle and TBI BR4404 treated rats. Adjusted p value: ****<0.0001.

There was a significant increase in % time freezing for the context trial in the TBI DIM Premix (BR4044) group as compared to TBI vehicle (p<0.0001) indicating superior learning. See FIG. 7.

Cue Fear Conditioning Analysis

Figure 8:
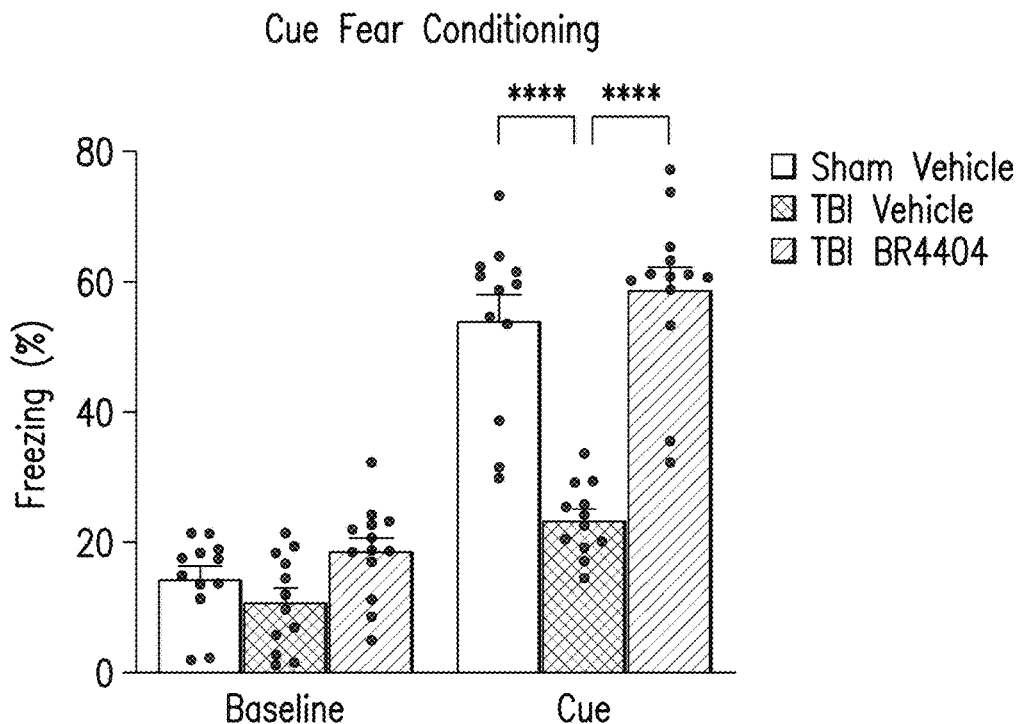
FIG. 8 shows Cue Fear Conditioning learning and memory measured as % freezing for sham vehicle, TBI vehicle and TBI BR4404 treated rats. Adjusted p value: ****<0.0001.

There was a significant increase in the % freezing time in the TBI DIM Premix (BR4044) group versus the TBI Vehicle group during the cue trial (p<0.0001). See FIG. 8.

Pathology Score Analysis

Hematoxylin and eosin-stained and NeuN-immunostained sections were scored from 0-4 for pathology between bregma levels −3 to −6 mm. Scoring was as follows:

0=no pathology

1=minor cell loss in either the parietal cortex, dentate hilus, or CA3 region of the hippocampus 2=cell loss in at least two regions: parietal cortex, dentate hilus, or CA3. Contusions only present in one cortical cell layer.

3=cell loss in at least two regions: parietal cortex, dentate hilus, or CA3. Contusions present in 2-3 cortical cell layers.

4=cell loss in all three regions: parietal cortex, dentate hilus, and CA3. Contusions present in 3 or more cortical cell layers.

Figure 9:
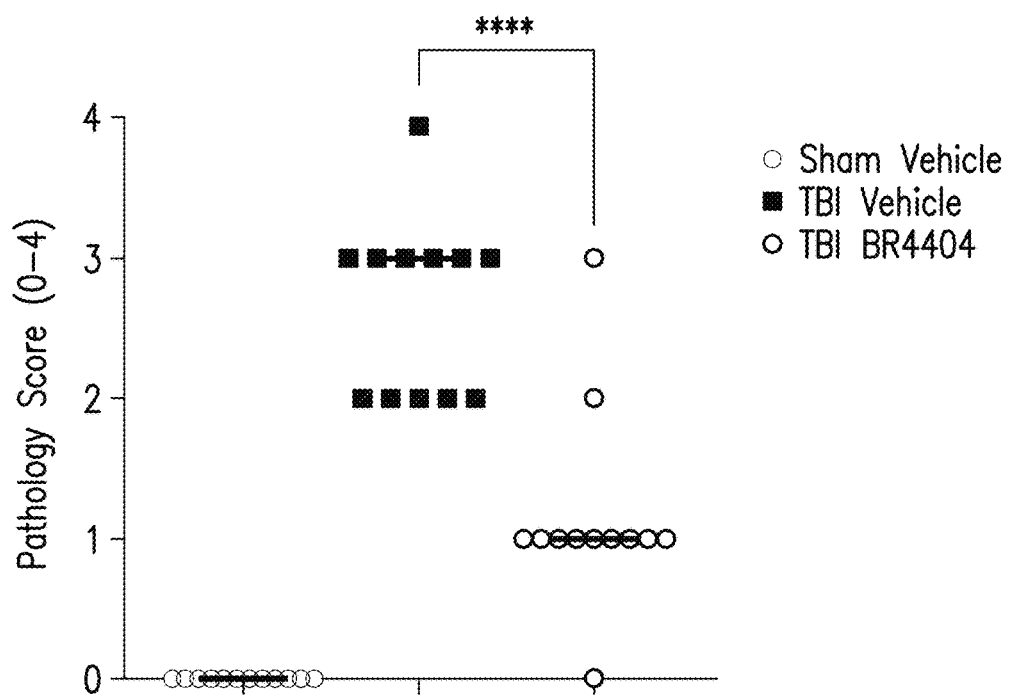
FIG. 9 shows the comparative cortical and hippocampal pathology score for sham vehicle, TBI vehicle and TBI BR4404 treated rats. Adjusted p value: ****<0.0001.

There was a significant decrease in the median pathology score in the TBI DIM Premix (BR4044) group compared to the TBI Vehicle (p<0.0001). The decrease in pathology was evident in the number of cortical contusions and neuronal loss in the parietal cortex and hippocampal dentate hilus and CA3 region. Note that all Sham Vehicle groups have a pathology score of 0 in accordance with the a priori exclusion criteria. See FIG. 9.

Representative Pathology Images of NeuN Immunostained Sections

Figure 10C:
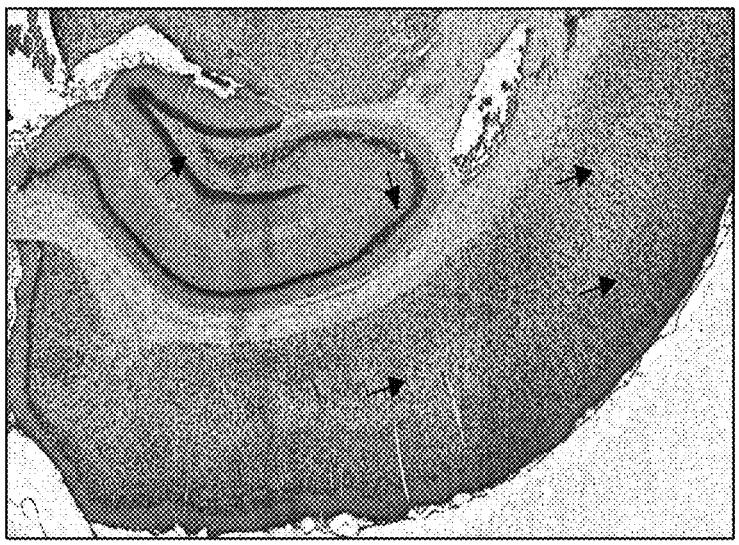
FIGS. 10A-C show representative pathology images of NeuN immunostained sections visualizing neuronal nuclear density in brains of sham vehicle (FIG. 10A), TBI vehicle (FIG. 10B) and TBI BR4404 (FIG. 10C) treated rats, respectively.
Figure 10B:
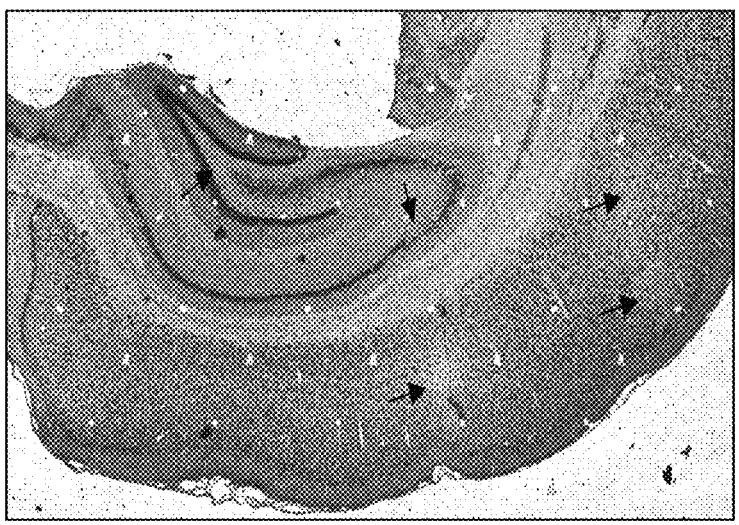
Figure 10A:
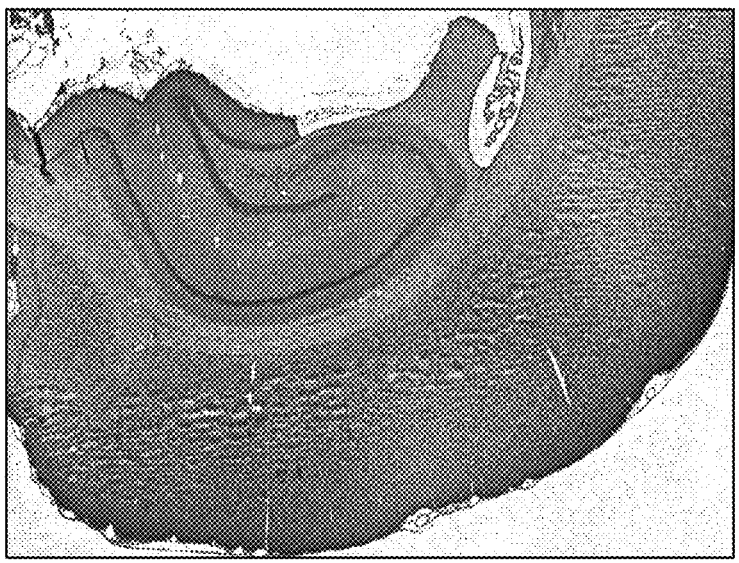

FIGS. 10A-C show representative pathology images of NeuN immunostained sections. There was visible neuronal loss in TBI Vehicle animals in the parietal cortex, dentate hilus, and CA3 region of the hippocampus (FIG. 10B arrows). These areas of neuronal loss are improved with DIM Premix (BR4044) treatment (FIG. 10C arrows).

FIG. 10A: The image represents the cortex and hippocampus of a Sham Vehicle animal at −3.3 mm posterior to bregma, stained with NeuN.

FIG. 10B: The image represents the cortex and hippocampus of a TBI Vehicle animal at −3.3 mm posterior to bregma, stained with NeuN.

FIG. 10C: The image represents the cortex and hippocampus of a TBI BR4044 animal at −3.3 mm posterior to bregma, stained with NeuN.

Extracellular Vesicle (EV) Analysis

Results showed that DIM treatment prevented the significant increase in EV numbers seen in untreated TBI animals at 24 hours after FPI. In addition, DIM treatment was associated with maintenance of a larger EV particle size which resembled the EV size found in uninjured Sham animals. See FIG. 11A-B.

FIG. 11A: EV particle size was significantly smaller in TBI Vehicle animals compared to Sham Vehicle animals (p=0.0023). Treatment with DIM Premix (BR4044) resulted in an increased size of the EV particles compared to untreated TBI animals (p=0.0117).

FIG. 11B: EV concentration was significantly greater in TBI Vehicle animals compared to Sham Vehicle animals (p=0.0415). Treatment with DIM Premix significantly decreased EV concentrations to Sham Vehicle levels (p=0.0415).

Post TBI Brain Contusion Volume

There was significantly less volume of Contusion Volume observed in the TBI DIM Premix (BR4044) treated animals at 10 days post FPI compared to TBI Vehicle control animals (p=0.0044). See FIG. 12.

Representative Pathology Images of Post TBI Contusions

Figure 13:
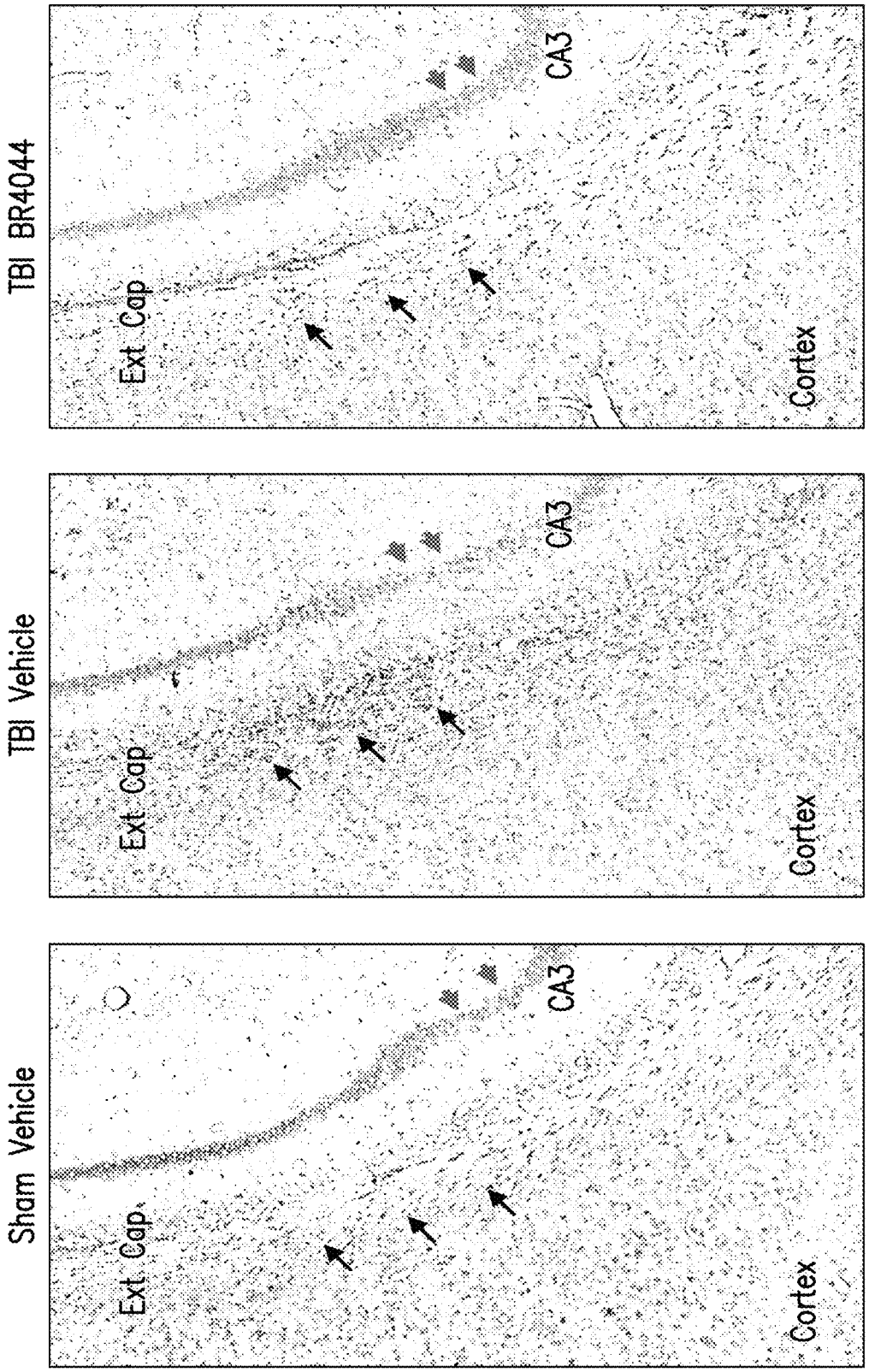
FIGS. 13A-C show representative H&E stained brain section pathology images of post TBI contusions for sham vehicle (FIG. 13A), TBI vehicle (FIG. 13B) and TBI BR4404 (FIG. 13C) treated rats.

Representative images show a visible cortical contusion in the TBI Vehicle example animal present within the external capsule (FIG. 13B, see arrows). Cortical contusion is not evident in the TBI BR4044 treated animal (FIG. 13C) and was similarly absent in 50% of the DIM treated animal group.

FIGS. 13A-C: The images are representative of the cortex and adjacent hippocampus for Sham (FIG. 13A), TBI Vehicle (FIG. 13B) and TBI BR4044 (FIG. 13C) animals at −3.3 mm posterior to bregma, stained with H&E and photographed at 10×magnification. Large Arrowheads denote normal CA3 cell body densities in the Sham Vehicle and TBI BR4044 images, whereas CA3 neuronal loss is visible in the TBI Vehicle image. The Small Arrows with Tails indicate a normal external capsule in the Sham Vehicle image, infiltration of inflammatory cells and disordered axonal tracts in the external capsule of the TBI Vehicle image and normal axonal tracts in the TBI BR4044 image.

Figure 14:
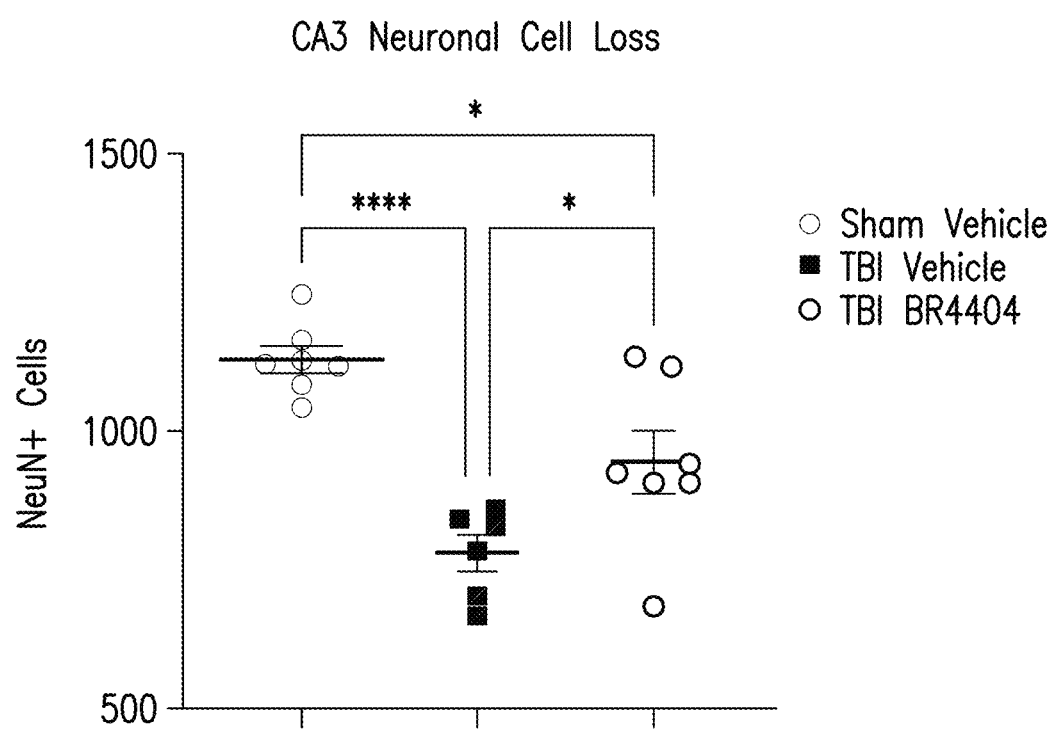
FIG. 14 shows CA3 Hippocampal Cell Loss data from NeuN+ stained neuronal cell counts from the CA3 hippocampal zone in sham vehicle, TBI vehicle and TBI BR4404 treated rats.

FIG. 14: CA3 Neuronal Cell Loss quantifying preservation of Hippocampal Neuronal Cells using NeuN immunostaining to identify and count neurons, there were significantly greater neuronal cell counts in the CA3 zone of the hippocampus in DIM Premix treated animals compared to Vehicle treated animals (p=0.0387).

Discussion and Conclusions

Diindolylmethane (DIM), delivered parenterally from diluted anhydrous DIM Premix, showed a significant treatment effect in the clinically relevant Lateral Fluid Percussion (LFP) model of TBI. The significant DIM treatment response included reduction in cortical and hippocampal edema and inhibition of the release of Extracellular Vesicles (EVs) at 24 hours past injury. Severity of cerebral edema and release of EVs at 24 hours post injury are both associated with poor clinical outcome in patients following TBI (Mondello S, Guedes V A, Lai C, Czeiter E, Amrein K, Kobeissy F, Mechref Y, Jeromin A, Mithani S, Martin C, Wagner C L, Czigler A, Tóth L, Fazekas B, Buki A, Gill J. Circulating Brain Injury Exosomal Proteins following Moderate-To-Severe Traumatic Brain Injury: Temporal Profile, Outcome Prediction and Therapy Implications. Cells. 2020 Apr. 15; 9(4):977.).

Using a limited 3 day treatment course emulating future, anticipated clinical use, a significantly reduced pathology score from histologic examination of brains was found in DIM treated animals at 10 days post injury. Neurobehavioral testing of animals 8 days after fluid percussion TBI showed more normal neurobehavioral outcome following DIM treatment compared to Vehicle treated TBI animals. Post TBI performance of DIM treated animals using the clinically relevant sensorimotor cylinder task and the contextual and cue fear conditioning tasks was significantly more normal than performance observed in the Vehicle treated control animals. Abnormal behavior involving sensorimotor and fear conditioning testing in rats has been correlated with the occurrence of cognitive and emotional dysfunction following TBI in humans. These disorders include anxiety disorders, especially post-traumatic stress disorder (PTSD), and cognitive dysfunction affecting learning and memory. The LFP injury model in rats is established as a translational model replicating the cognitive and emotional effects of TBI in humans (Reger M L, Poulos A M, Buen F, Giza C C, Hovda D A, Fanselow M S. Concussive brain injury enhances fear learning and excitatory processes in the amygdala. Biol Psychiatry. 2012 Feb. 15; 71(4):335-43.).

The improved neurobehavioral performance of DIM treated TBI animals at 8 days post injury correlated to the reduced presence of neuroanatomic histopathology in the same animals. Quantification of brain Contusion Volume at day 10 post injury was statistically less in DIM treated TBI animals than in vehicle treated TBI animals at 10 days following FPI. The complete absence of measurable Contusion Volume following FPI in 50% of the DIM treated animals is surprising and has not been reported previously using similar fluid percussion injury in rats treated with other agents. At the cellular level, cell counting of hippocampal neurons using NeuN histochemical staining showed significantly greater numbers of CA3 zone hippocampal neurons following DIM treatment compared to the CA3 zone neurons counted in post injury vehicle animals. Following FPI the CA3 zone is known to suffer the most severe cellular injury and neuron loss. This portion of the hippocampus is known to be critical for the encoding and retrieval of memories. Damage to this hippocampal region is linked to memory and cognitive deficits (Giordano K R, Law L M, Henderson J, Rowe R K, Lifshitz J. Time Course of Remote Neuropathology Following Diffuse Traumatic Brain Injury in the Male Rat. Exp Neurobiol. 2022 Apr. 30; 31(2):105-115). Preservation of neuronal cells in the CA3 hippocampal zone by DIM treatment following TBI in rats provides a basis for clinical success for the analogous use of DIM drug products to prevent cognitive dysfunction following TBI in humans.

Taken as a whole, the present results evaluating the activity of DIM in a translatable TBI model indicate that DIM provides a new therapeutic agent for the clinical treatment of TBI, encompassing NHCHI, which provides inhibition of pathogenic EV release and supports improved neurobehavioral outcome.

This disclosure is not to be limited in scope by the embodiments disclosed in the examples which are intended as single illustrations of individual aspects, and any equivalents are within the scope of this disclosure. Various modifications in addition to those shown and described herein will become apparent to those skilled in the art from the foregoing description. Such modifications are intended to fall within the scope of the appended claims.

Various references such as patents, patent applications, and publications are cited herein, the disclosures of which are hereby incorporated by reference herein in their entireties.

What is claimed is:

1. A method of treating non-hemorrhagic closed head injury (NHCHI) in a subject, comprising administering to the subject 3,3'-diindolylmethane (DIM) and, optionally, further comprising administering to the subject a second active agent.

2. The method of claim 1, wherein the DIM is administered intravenously or intrathecally.

3. The method of claim 1, wherein the DIM is administered orally.

4. The method of claim 3, wherein the DIM is formulated in a self-micro-emulsifying drug delivery (SMEDD) formulation.

5. The method of claim 1, wherein the second active agent is selected from glycyrrhizin, diammonium glycyrrhizinate, amantadine, metformin, melatonin, aripiprazole, brexpiprazole, clozapine, risperidone, olanzapine, quetiapine, lumateperone, ziprasidone, paliperidone, asenapine, iloperidone, lurasidone, chloroquine, hydroxychloroquine, sodium selenite pentahydrate, selenious acid, IC-100 monoclonal antibody and combinations thereof.

6. The method of claim 1, wherein the NHCHI is mild (mTBI) to severe concussion, blast injury due to proximity to explosions, cerebral contusion, coup-contrecoup injury, Diffuse Axonal Injury, Second Impact Syndrome, or CHI associated with deceleration injury.

7. The method of claim 1, wherein the subject has undergone an imaging procedure which has ruled out intracranial hemorrhage.

8. The method of claim 1, wherein the subject has regained consciousness following a coma and has no lateralizing signs on neurologic examination.

9. The method of claim 1, wherein the subject is suspected of having increased intracranial pressure for whom treatment with mannitol is contra-indicated.

10. The method of claim 3, wherein the subject is conscious.

11. The method of claim 2, wherein the subject is a stuporous or sedated patient.

12. The method of claim 10, wherein the composition and dosage is a self-micro-emulsifying drug delivery (SMEDD) DIM formulation providing 200-500 mg DIM per oral administration in adults, repeated after 4-8 hours three times and thereafter every 12 hours for 3-5 days.

13. The method of claim 11, wherein intravenous (IV) or direct to CSF administration of DIM is from an intravenous DIM premix drug product.

14. The method of claim 13, wherein the dosage of IV or direct to CSF DIM is from 25-200 mg DIM administered with a 30-minute infusion, repeated after 4-8 hours three times and thereafter every 8-12 hours for up to 3-5 days.

15. The method of claim 14, wherein the IV or direct to CSF composition of DIM is administered when used in conjunction with mannitol.

16. A method of preventing or limiting an increase in increased intracranial pressure in a subject with non-hemorrhagic closed head injury (NHCHI), comprising co-administering (i) 3,3'-diindolylmethane (DIM), and (ii) mannitol to the subject.

* * * * *